(12) United States Patent
Kaloudis et al.

(10) Patent No.: US 10,614,403 B2
(45) Date of Patent: Apr. 7, 2020

(54) METHODS FOR POST-HARVEST CROP QUALITY MANAGEMENT

(71) Applicant: Centaur Analytics, Inc., Ventura, CA (US)

(72) Inventors: Efstathios Kaloudis, Athens (GR); Sotirios Bantas, Volos (GR); Vasileios Sotiroudas, Salonika (GR); Ronald E. Ham, Austin, TX (US)

(73) Assignee: Centaur Analytics, Inc., Ventura, CA (US)

( * ) Notice: Subject to any disclaimer, the term of this patent is extended or adjusted under 35 U.S.C. 154(b) by 31 days.

(21) Appl. No.: 15/968,516

(22) Filed: May 1, 2018

(65) Prior Publication Data

US 2018/0320967 A1 Nov. 8, 2018

Related U.S. Application Data

(60) Provisional application No. 62/500,294, filed on May 2, 2017.

(51) Int. Cl.
*G01N 33/00* (2006.01)
*G06Q 10/06* (2012.01)
(Continued)

(52) U.S. Cl.
CPC ....... *G06Q 10/06395* (2013.01); *A01D 91/00* (2013.01); *A01F 25/22* (2013.01); *A01M 1/026* (2013.01); *F26B 9/063* (2013.01); *F26B 21/10* (2013.01); *G01N 27/4162* (2013.01); *G01N 33/004* (2013.01); *G01N 33/0075* (2013.01); *G01N 33/025* (2013.01); *G06F 17/13* (2013.01); *G06F 17/5009* (2013.01);
(Continued)

(58) Field of Classification Search
None
See application file for complete search history.

(56) References Cited

U.S. PATENT DOCUMENTS 4,688,332 A * 8/1987 Kallestad .............. F26B 3/06
 34/491
4,930,229 A * 6/1990 Moser .................. F26B 9/063
 34/491

(Continued)

OTHER PUBLICATIONS

A. Kaleta and K. Gornicki,"Criteria of Determination of Safe Grain Storage Time—A Review" pp. 295-318, (Year: 2013).*

(Continued)

*Primary Examiner* — Kibrom K Gebresilassie
(74) *Attorney, Agent, or Firm* — Ascenda Law Group, PC

(57) ABSTRACT

Embodiments of systems and approaches for managing post-harvest crop quality and pests are described. Such a system may include a plurality of edge devices each comprising sensor components and collectively forming a mesh network, for measuring the local physical environment within stored crops and, for example, transmitting the measurements to a service from within the crop storage area. In certain embodiments, such a system may be used to manage post-harvest crops and storage areas—for example, approaches are described for determining fumigation treatment duration, determining phosphine dosage, determining heat treatment duration, and determining safe storage time for crops.

5 Claims, 23 Drawing Sheets

(51) Int. Cl.
<table>
<tr><td>G06Q 50/02</td><td>(2012.01)</td></tr>
<tr><td>G06F 17/13</td><td>(2006.01)</td></tr>
<tr><td>G06F 17/50</td><td>(2006.01)</td></tr>
<tr><td>G01N 27/416</td><td>(2006.01)</td></tr>
<tr><td>G01N 33/02</td><td>(2006.01)</td></tr>
<tr><td>A01D 91/00</td><td>(2006.01)</td></tr>
<tr><td>A01F 25/22</td><td>(2006.01)</td></tr>
<tr><td>A01M 1/02</td><td>(2006.01)</td></tr>
<tr><td>F26B 9/06</td><td>(2006.01)</td></tr>
<tr><td>F26B 21/10</td><td>(2006.01)</td></tr>
<tr><td>G06Q 10/08</td><td>(2012.01)</td></tr>
<tr><td>G08C 17/02</td><td>(2006.01)</td></tr>
<tr><td>A01M 13/00</td><td>(2006.01)</td></tr>
</table>

(52) U.S. Cl.
CPC ..... *G06Q 10/06315* (2013.01); *G06Q 10/087* (2013.01); *G06Q 50/02* (2013.01); *G08C 17/02* (2013.01); *A01M 13/00* (2013.01); *G01N 33/02* (2013.01); *G06F 2217/16* (2013.01)

(56) References Cited

U.S. PATENT DOCUMENTS

<table>
<tr><td>8,596,194</td><td>B2 *</td><td>12/2013</td><td>Kraus</td><td>A01F 15/08<br>100/2</td></tr>
<tr><td>9,140,824</td><td>B1 *</td><td>9/2015</td><td>Mewes</td><td>A01B 79/005</td></tr>
<tr><td>9,986,690</td><td>B2 *</td><td>6/2018</td><td>Younk</td><td>A01F 15/08</td></tr>
<tr><td>2004/0212509</td><td>A1 *</td><td>10/2004</td><td>Zweig</td><td>G01K 3/04<br>340/588</td></tr>
<tr><td>2010/0257125</td><td>A1 *</td><td>10/2010</td><td>Kallestad</td><td>A01F 25/22<br>705/418</td></tr>
<tr><td>2012/0103205</td><td>A1 *</td><td>5/2012</td><td>Kraus</td><td>A01F 15/08<br>100/2</td></tr>
<tr><td>2016/0117783</td><td>A1 *</td><td>4/2016</td><td>Singh</td><td>G06Q 30/018<br>705/317</td></tr>
<tr><td>2017/0270616</td><td>A1 *</td><td>9/2017</td><td>Basso</td><td>A01B 79/005</td></tr>
<tr><td>2017/0311559</td><td>A1 *</td><td>11/2017</td><td>Ebert</td><td>A01G 22/00</td></tr>
<tr><td>2018/0052437</td><td>A1 *</td><td>2/2018</td><td>Leonelli</td><td>H04W 4/38</td></tr>
<tr><td>2018/0316725</td><td>A1 *</td><td>11/2018</td><td>Mani</td><td>H04L 63/20</td></tr>
<tr><td>2018/0330247</td><td>A1 *</td><td>11/2018</td><td>Cohen</td><td>G06F 16/22</td></tr>
</table>

OTHER PUBLICATIONS

W. Zhou, "Endogenous Price in a Dynamic Model for Agricultural Supply Analysis" May 2014, p. 1-35. (Year: 2014).*

"Fumigating with phosphine, other fumigants and controlled atmospheres: A grains industry guide", GRDC, Grains Research and Development Corporation (2011), 16 pages.

"Phosphine fumigation parameters for the control of cigarette beetle and tobacco moth", CORESTA, CORESTA guide No. 2 (Oct. 2013), 4 pages.

Adelard; et al., "Sky temperature modelisation and applications in building simulation", Renewable Energy (1998), 15(1):418-430.

Ahmad; et al., "Effect of the key mixture parameters on tortuosity and permeability of concrete", Journal of Advanced Concrete Technology (Mar. 2012), 10:86-94.

Barreto; et al., "Analysis of storage conditions of a wheat silo-bag for different weather conditions by computer simulation", Biosystems Engineering (2013), 116:497-508.

Collins; et al., "Response of mixed-age cultures of phosphine-resistant and susceptible strains of lesser grain borer, rhyzopertha dominica, to phosphine at a range of concentrations and exposure periods", Journal of Stored Products Research (2005), 41:373-385.

Darby, J. A., "A kinetic model of fumigant sorption by grain using batch experimental data", Pest Management Science (2008), 64(5):519-526.

Driscoll; et al., "Prediction of insect populations in grain storage", Journal of Stored Products Research (2000), 36(2)131-151.

Fleurat-Lessard, F., "Integrated management of the risks of stored grain spoilage by seedbome fungi and contamination by storage mould mycotoxins—An update", Journal of Stored Products Research (2017), 71:22-40.

He; et al., "Gas transport in oxide fuel cells", Springer Briefs in Energy, Springer International Publishing (2014), New York, USA, 87 pages.

Isa; et al., "Mathematical modelling and numerical simulation of phosphine flow during grain fumigation in leaky cylindrical silos", Journal of Stored Products Research (2016), 67:28-40.

Kaleta; et al., "Criteria of Determination of Safe Grain Storage Time—A Review", Advances in Agrophysical Research (2013), Chapter 12, pp. 295-318.

Lawrence; et al., "Three-Dimensional Transient Heat, Mass, Momentum, and Species Transfer in the Stored Grain Ecosystem: Part I. Model Development and Evaluation", Transactions of the ASABE (2012), 56(1):179-188.

McQuillan; et al., Properties of Dry Air as One Atmosphere, Microelectronics Heat Transfer Lab. (Jun. 1984), Rept UW /M HTL 8406 G-01, Univ. of Waterloo, Waterloo, ON, Canada, 5 pages.

Neethirajan; et al., "Investigation of 3d geometry of bulk wheat and pea pores using x-ray computed tomography images", Computers and Electronics in Agriculture (2008), 63(2):104-111.

Paparrizos; et al., "k-Shape: Efficient and Accurate Clustering of Time Series", ACM SIGMOD Record (2016), 45(1):69-76.

Robinson, J.R., "Residues containing phosphorus following phosphine treatment: Measurement by neutron activation", Journal of Stored Products Research (1972), 8(1):19-26.

Shen; et al., "Critical review of the impact of tortuosity on diffusion", Chemical Engineering Science (2007), 62(14):3748-3755.

* cited by examiner

900

902

⌂ > Activities > Treatment Plans > Treatment - 08/05/2017 12:16
Treatment - 08/05/2017 12:16

Dashboard

Activities          ⚙ Edit Treatment Plan ⓘ   903

Processes           ─ General ──────────────────────────────────────────
                    Treatment Type*              904              Description*
Recipes             Phosphine Treatment                           ▽ Treatment - 08/06/2017 12:16

Assets              ─ Asset ────────────────────────────────────────────
                    Asset*                       906              Fill Percentage (%)*         🖩
Devices             silo-1
                    Location: London, England, United Kingdom ⓘ   ▽ 30.41            ⓘ
Settings            Volume: 125.66 m³                             Stored Product: Wheat, Whole
                    Quick edit asset                              Product Quantity: 30000 kg ─ Pests ────────────────────────────────────────────  ⓘ
                    Pest Type*                   908
                    Tribolium castaneum (Red Flour Beetle), Tribolium confusum (Confused Flour Beetle), Sitophilus Granarius (Wheat Weevil) ▽
                    ☐ Not sure which insect
                    Are pests resistant to treatment?
                    ● Yes ○ No  ⓘ

─ Treatment ────────────────────────────────────────
                    Phosphide*                   910                                    ▽ Recommend
                    Magnesium bags (11,314 g of Phosphine/item)
                    Quantity
                    ● Dosage ○ Items  ⓘ
                    Dosage g/m³                                   ⓘ Total Items Quantity
                    0.63                                              7
                    Info: 7 Magnesium bags in 125.66 m³, release 0.63 g of Phosphine per m³

Calculate & Update

☆ > Activities > Treatment Plans > Treatment - 12/06/2017 09:58
Treatment - 12/06/2017 09:58

Edit Treatment Plan ⓘ  903

General
Treatment Type*           904          Description*
Phosphine Treatment                    ▽ Treatment - 12/06/2017 09:58

Asset
Asset*                    906          Fill Percentage (%)*
Container 34                           ▽ 100
Location: Volos, Magnesia Prefecture, Greece ⓘ    Stored Product: Tobacco (Cigarette)
Volume: 67.57 m³                       Product Quantity: 25000 kg
*Quick edit asset*

Pests
Pest Type*                908
Ephestia Elutella (Tobacco Moth)
☐ Not sure which insect
Are pests resistant to treatment?
○ Yes ○ No ⓘ

Product Conditions         1002
Expected Leakage
○ No ○ Low ○ High ⓘ

Temperature                              Relative Humidity
  Temperature*                             Relative Humidity
  19           °C                          65           %
○ Weather                                ○ Weather
○ Sensor                                 ○ Sensor
○ Manual                                 ○ Manual 902
Dashboard
Activities
Processes
Recipes
Assets
Devices
Settings

FIG. 10A

METHODS FOR POST-HARVEST CROP QUALITY MANAGEMENT

CROSS REFERENCE TO RELATED APPLICATIONS

This nonprovisional application claims the priority benefit of U.S. Provisional Patent Application No. 62/500,294, filed on May 2, 2017, the disclosure of which is incorporated herein by reference in its entirety.

TECHNICAL FIELD

The disclosed embodiments relate generally to post-harvest crop management, and more particularly, to methods and systems for managing crop quality and pests, e.g., using agricultural sensors, data analytics, crop storage and pest management techniques.

BACKGROUND

For centuries the global food and agriculture industry has tolerated significant post-harvest waste, presently estimated at approximately $1 trillion annually. World population is expected to reach 10.5 billion by 2050, further exacerbating global food availability and security concerns. According to research data, food supplies would need to increase by 60% (estimated at 2005 food production levels) in order to meet the food demand by 2050. Food availability and accessibility can vastly improve by increasing production, enhancing logistics, and reducing waste. Thus, reduction of post-harvest waste is a critical component of ensuring future global food security.

Additionally, health and safety concerns feature high on the agendas of governments and regulators. In this respect, the application of agrichemicals needs to be monitored with advanced technology, to ensure proper use (adherence to precise pest control protocols), environmental safety (managing stored product pests and controlling tolerance and resistance to pesticides) and operator safety (controlling leaks of harmful toxic substances).

End users in this field, such as farmers, operators of storage and logistics facilities, agronomists, food scientists, pest control technicians and quality control experts, have used certain methods in the prior art to combat post-harvest waste and its root causes including pest infestations. These methods have employed technology conceived several decades ago, to perform functions such as fumigation chemical (i.e. fumigant) dosage monitoring, insect infestation detection, spoilage detection. Our assessment revealed that none of these legacy solutions and methods in the prior art effectively addressed the trillion-dollar waste problems. Moreover, prior art methods for post-harvest monitoring and quality control have also been manual, error-prone, cumbersome, not scalable, outdated and impractical. They have also been costly without resultant benefits. Specifically:

- Draeger-type fumigant meters have the form of tubes. These require a lot of manual effort by experienced operators. There are hazards related to their use. Data is typically recorded by pen and paper.
- Certain electronic equipment vendors are offering measurement devices for fumigation monitoring. These require special plumbing for sampling fumigant levels inside storage areas, are difficult to operate and are usually practical only for infrequent sampling. The data collected is not practically correlated with proper fumigation protocols or insect mortality statistics.
- Certain crop silo monitoring solutions focus specifically on temperature tracking to detect spoilage as it occurs. They employ old technology (wired thermocouples) and are difficult to install. They also malfunction or get completely destroyed in the presence of fumigant gas. Consequently, when a spoilage hotspot is detected, it is usually already too late to take corrective action.
- Insect collectors and detectors such as pheromone traps require manual inspection. Electronic products for insect detection that can transmit insect population data cannot be placed inside bulk product where insects may take refuge. The data collected is not correlated with pest management parameters (such as recent fumigation dosages and durations) or environmental conditions (such as temperature, humidity).
- Certain methods in the prior art provide computational means for assessing properties related to the spoilage of crops (such as grains) in storage, by estimating key parameters such as product moisture based on parameters that can be readily observed (such as product temperature and ambient relative humidity). However, these tools are of limited accuracy and usefulness as storage microclimate may change unpredictably (e.g. during a hot and humid weather spell) and thus render any initial estimates invalid. Moreover, the initial conditions of a stored product may not be fully known— e.g. unknowingly mixing a quantity of damp and infested grain with a larger quantity of drier and good quality grain may spread the spoilage and infestation to the entire lot of grain.
- Researchers in this field have resorted to numerical analysis techniques such as Computational Fluid Dynamics (CFD) simulations to predict the effects of climate conditions on stored commodities. However, these visionary approaches have not materialized into convenient and handy tools for the actual end user (who is typically not expert in numerical analysis) as they have been overly complicated, not easy to control and re-use and not generic enough to address a good variety of commodity storage scenarios. Besides, these techniques have fallen short of correlating concurrently updated physical parameters with biological effects related to grain spoilage and quality degradation.

BRIEF DESCRIPTION OF THE DRAWINGS

FIG. 9A and FIG. 9B show an exemplary post-harvest crop management user interface in accordance with some embodiments of the invention;

FIG. 10A and FIG. 10B show an exemplary post-harvest crop management user interface in accordance with some embodiments of the invention;

DETAILED DESCRIPTION

Embodiments of apparatuses, computer systems, computer readable mediums, and methods for post-harvest crop quality and pest management are described. For example, embodiments described herein provide a solution that effectively combats spoilage root causes, such as mycotoxins and insects, and guides end users to efficient pest management in post-harvest storage of agricultural commodities. The solution may be based on cloud-connected wireless sensors, real-time data monitoring, data analytics and computational fluid dynamics simulations.

Embodiments described herein effectively resolve the shortcomings of previous strategies, to provide efficient post-harvest crop and food product protection and quality management. It efficiently addresses the $1 trillion waste root causes and brings benefits that can positively and dramatically impact food safety and agriproduct abundance in the future. The inventions achieve these goals by providing fully automated, real-time, in situ (i.e. inside product storage areas) monitoring of fumigants and storage conditions, by coupling sensors with data analytics and cognitive methods, and by thus driving predictions and prescriptions of fumigant distribution, pest treatment parameters, insect mortality and repopulation, spoilage risks, stored crops quality metrics and several other related parameters and end user guidelines.

As described below, edge devices containing sensors may be used to directly measure physical descriptors in situ. The edge devices preferably support self-organizing, ad-hoc mesh networking (e.g., to avoid the need for fixed infrastructure) and may be designed in such a way to comply with the needs in the various industrial and, often, harsh environments in which they function, both in terms of mechanical and electronic robustness but also in terms of wireless communication.

Computational fluid dynamics approaches described below permit predicting granular fumigation treatment durations and recommended dosages for new crop storage areas, even when no historical data is available. The analytical approaches described below include monitoring and guiding heat treatments by detecting anomalies and alarm conditions, replacing and coping with incorrect sensor readings, with the benefit of being computationally efficient and accordingly taking less time to obtain results.

Further, this system can achieve further unsupervised learning by correlating real-time insect population data to fumigant levels. Additionally, we can combine CFD simulation with sensor data and automatically (i.e. via machine learning methods) adjust the correction factors in CFD to match actual data streams, and subsequently use the 'trained' CFD simulation to make accurate long-term predictions. This applies to both predictive pest management and crop spoilage detection use cases.

Figure 1:
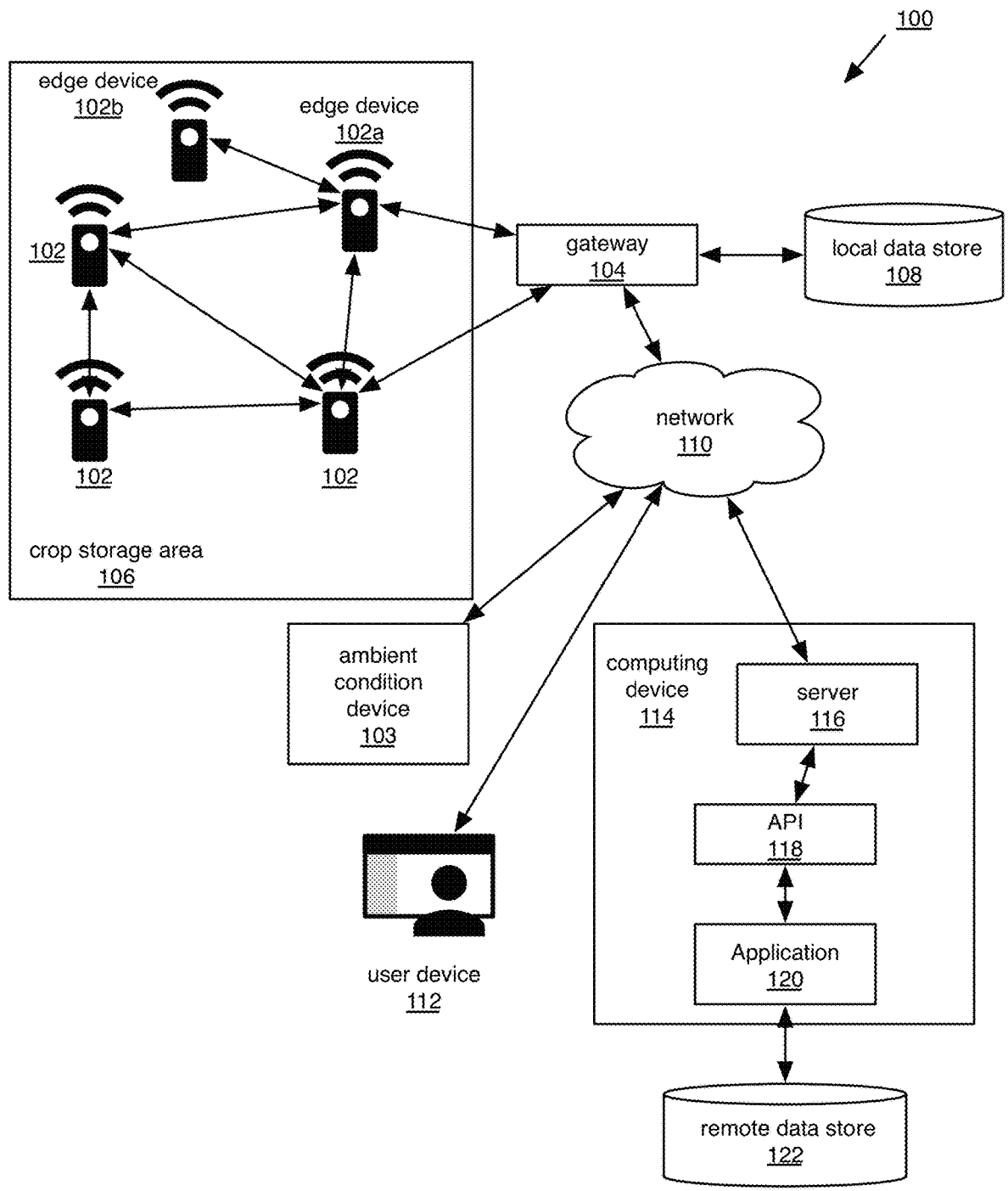
FIG. 1 depicts an exemplary post-harvest crop management system in accordance with some embodiments of the invention.

FIG. 1 depicts an exemplary post-harvest crop quality and pest management system 100. Components of system 100 may be positioned relative to a crop storage area 106 for storing a harvested crop, such as rice or wheat. A collection of edge devices 102 may be placed within the crop storage area 106, such that they may be used to measure physical features (e.g., temperature or gas concentration) of the environment local to each respective edge device 102 in different locations within the crop storage area. For example, edge devices may be mounted to the walls of the storage area, suspended on wires such that the edge devices are buried within bulk crop (e.g., surrounded by grains), and/or positioned between containers of crops or agricultural materials such as sacks of flour. Wires or other attachments may be used in order to easily retrieve the edge devices as needed, e.g., upon completion of a fumigation.

In system 100, the edge devices 102 are configured to form a wireless ad hoc network, such as a mesh network, to wirelessly transmit data including the measurements concerning the local environment to a network 110 via a gateway device 104 for connecting the network of edge devices to network 110. Each edge device 102 may be associated with a unique identifier that can be associated with the measurements made by the respective device, in order to correlate the measurements with a location within the crop storage area. When the edge devices are configured as a mesh network, data transmission from within the crop storage area is robust, as multiple wireless connections between the edge devices provide redundancy in such a topology. For example, one or more edge devices (e.g., 102a) may act as a relay, providing an indirect communication link between other edge devices (e.g., 102b) and the gateway device 104. Because of their shared design configurations, any individual edge device 102 may function as a relay. In certain embodiments, system 100 includes local data store 108, communicatively coupled to the gateway 104, for maintaining an on-site back-up for the measurement data from the edge devices. Additional discussion regarding wireless transmission is provided below, for example in connection with FIG. 6.

Network 110 may be a conventional computer network and/or network of networks (e.g., a local area network, wide area network, and/or the Internet). In certain embodiments, one or more computing devices 114 communicatively coupled to the gateway 104 over network 110 hosts a server 116, such as an HTTP server, and an application 120 that implements aspects of the post-harvest crop quality and pest management system in accordance with embodiments of the present invention. Application 120 may perform analytics on measurement data received from gateway 104, and stores same, preferably along with copies of the measurement data, in a remote data store 122. Remote data store 122 may be a dedicated storage appliance, or may be cloud-based storage accessible to computing device 114.

Application 120 may support an Application Programming Interface (API) 118 providing external access to methods for initiating analyses and accessing remote data store 122 via server 116. In certain embodiments, client applications such as web browsers running on user device(s) 112 may access application 120 via its API 118 and through server 116 using protocols such as HTTP or FTP (see, e.g., FIGS. 9-11 showing exemplary user interfaces for a user device 112 discussed in detail below). In certain embodiments, user device 112 may be a laptop or desktop computer, a mobile device such as a smart phone, or a wearable device such as a smart watch.

Edge Device

Figure 2A:
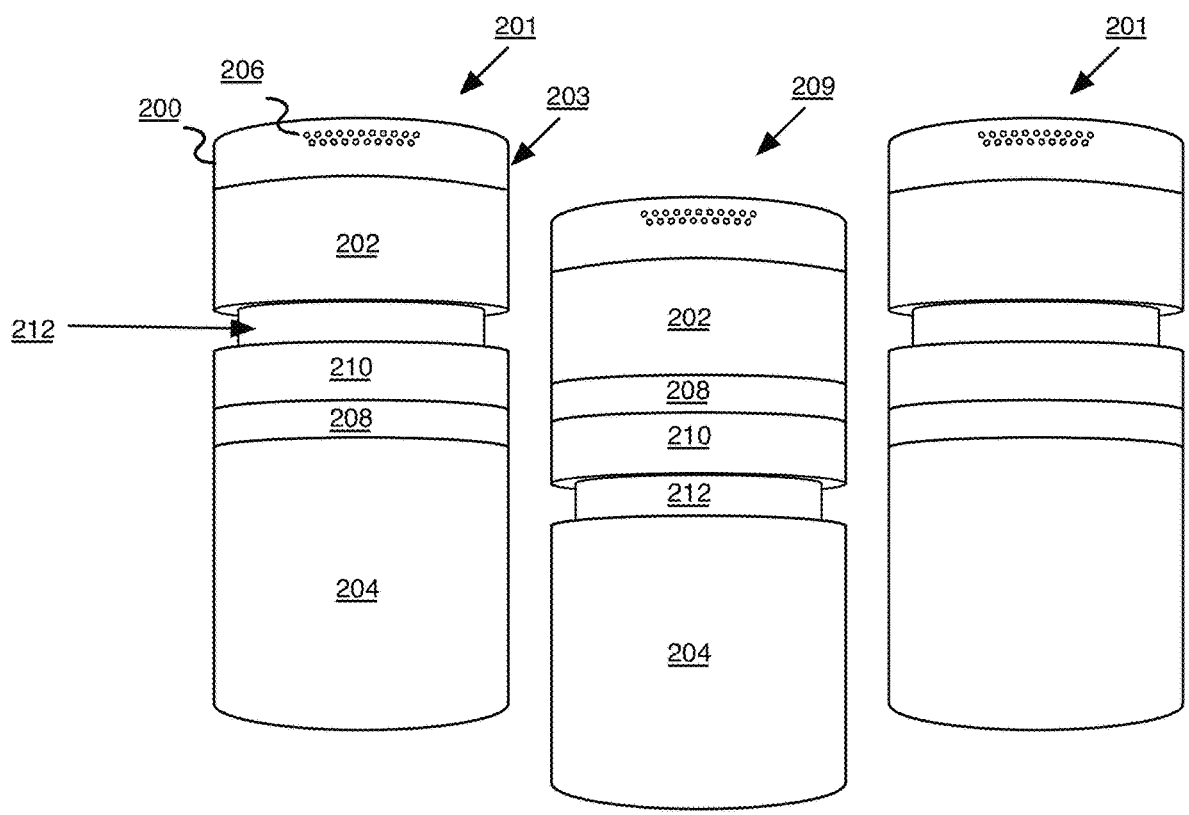
FIG. 2A and FIG. 2B depict exemplary edge devices in accordance with some embodiments of the invention.
Figure 2B:
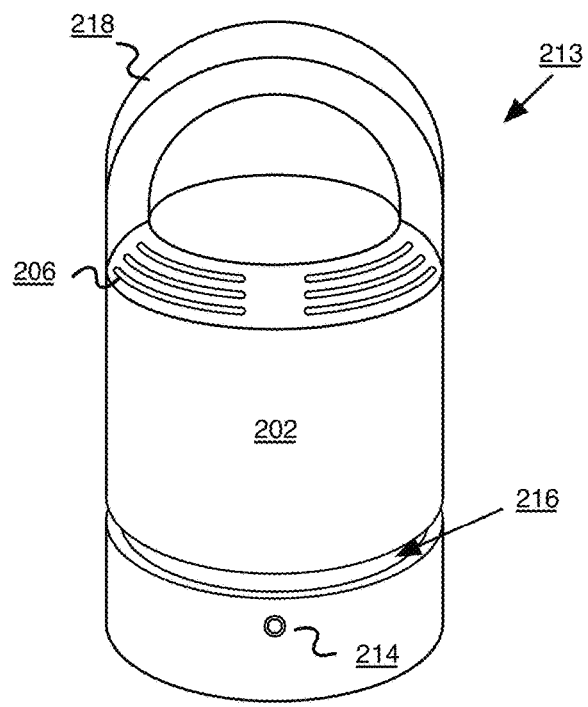

FIG. 2A depicts embodiments 201 and 209 of edge device 102, and FIG. 2B depicts an embodiment 213 of edge device 102. As used herein, edge devices 102 are devices that are configured to take measurements of physical attributes of the environment local to the respective edge device, and are configured as a group to form a wireless ad hoc network, such as a mesh network, to wirelessly transmit data including the measurements. In certain embodiments, edge devices are more specifically configured to have certain additional features as described throughout this specification. Embodiment 201 has a generally cylindrical housing. In certain embodiments, the housing includes vents 206 which are openings allowing air surrounding the edge device to diffuse into and out of a chamber within the cap 200, permitting detection of, e.g., moisture content and/or gases within the environment local to the edge device (e.g., at a location within crop storage area 106). In certain embodiments, the vents 206 are two or more holes or pores arranged in a grid. In certain embodiments, the vent holes are one or more circular or oval-shaped holes. In certain embodiments, the vents are micro holes—i.e., with a diameter in the tens of micrometers. In certain embodiments, the vents may be shaped like a curved slit (e.g., as shown in embodiment 213 in FIG. 2B) or straight slit, where the slit has a length of about half a millimeter. In certain embodiments, a particular vent configuration (e.g., regarding hole number, size, shape, and/or layout) may be used for a corresponding type of measurement such that a housing with a first vent arrangement is used for, e.g., phosphine concentration sensing, and a second housing with a second vent arrangement is used for, e.g., humidity sensing. For example, particular vent configurations can improve sensor accuracy and a faster return to zero gas by facilitating the flow of the target gas over a sensor's active surface. In certain embodiments, a single vent configuration may be optimized for two or more sensing tasks (e.g., phosphine and humidity sensing).

The housing 203 may be assembled from components such as the cap 200 that mates with an upper housing 202, the upper housing connecting to a lower housing 204. In certain embodiments, the cap, upper housing, and lower housing are threadibly coupled to one another, for example via a first threaded portion of the cap 200 mating with a second threaded portion of the upper housing 202, and a third threaded portion of the upper housing 202 mating with a fourth threaded portion 212 of the lower housing 204. In other embodiments, bayonet couplings, compression couplings, pin-and-groove couplings, or combinations thereof may be used instead of, in addition to, or in combination with threaded couplings. Static couplings are preferred, in order to provide rigidity to the overall housing, but in some circumstances flexible couplings may be employed for situations where edge devices need to conform to specific recesses or other areas in a crop storage area. In certain embodiments, connections between components of the housing may be permanently sealed, or may reversibly join together.

In certain embodiments, the edge device 102 may include a magnetic ring 208 and a switch suppress ring 210. Magnetic ring 208 is a circumferential ring that includes a magnet. The magnetic ring 208 is mounted on a bearing or other surface and allowed to swivel, at least partially, azimuthally around the housing 203. In this way, the associated magnet is translated circumferentially and, as discussed below, will cause a Reed switch inside the housing to open or close, depending on the direction of movement. The opening and closing of the Reed switch will turn the edge device off and on, respectively. In other embodiments, the magnetic ring may be fashioned to be translated vertically, parallel to the longitudinal axis of the edge device, and thereby control the opening and closing of the Reed switch. However, in such embodiments, detents should be provided, or a sufficient friction fit maintained, so that the magnetic ring does not translate between its open and closed positions unintentionally. In still further embodiments, a magnetic ring may be omitted in favor of a capacitive or resistive switch that is used to control the operational state of the edge device (e.g., according to a user's touch operation).

The housing 203 components (e.g., cap 200, upper and lower housing 202 and 204 of embodiment 201) and portions of the magnetic ring and switch suppress ring may be formed from a material such as plastic (e.g., an acetal plastic such as an acetal copolymer or acetal homopolymer). In certain embodiments, the material used for the housing should be corrosion-resistant in order to protect the internal electronics and other components from toxic gases used in agricultural fumigation. Desirable properties of the housing material include, for example, resistance to high- and low-pH solutions (e.g., fuels and solvents), low porosity, high stability, and minimal sensitivity to high and low temperatures.

FIG. 2B shows an exemplary embodiment 213 of an edge device 102, in which the housing is largely bell-shaped and includes a handle 218. The edge device may include an indicator band 216 and an indicator light 214. Indicator bands and lights may turn on or off or change color to indicate the operational status of the edge device—for example, the indicator may flash or turn on to indicate states such as: the edge device is on, is collecting data, is transmitting data, is ready to pair with a network, is performing a firmware update, or is in an error state.

Figure 3:
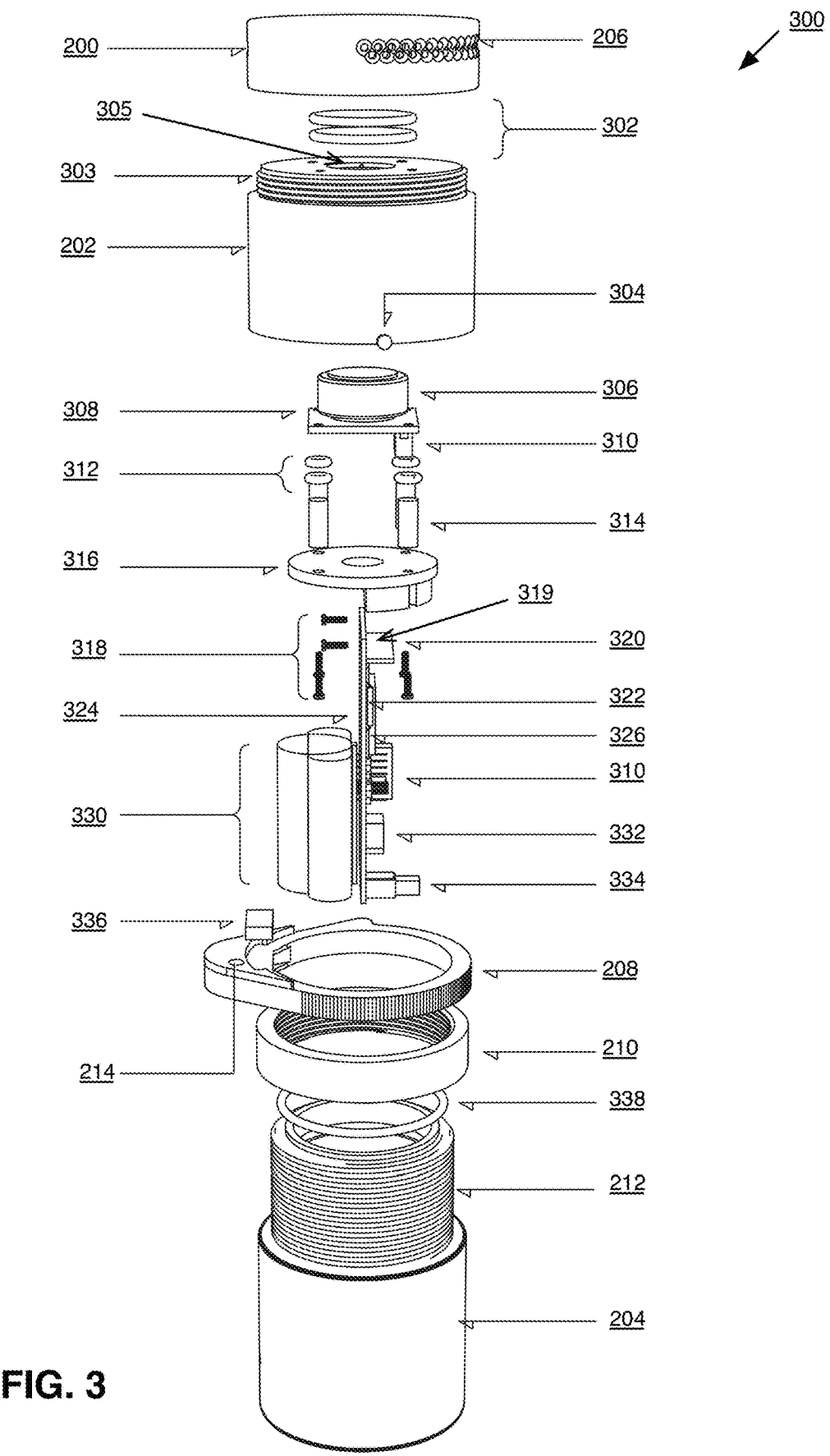
FIG. 3 depicts an exploded view for an exemplary edge device in accordance with some embodiments of the invention.
Figure 4:
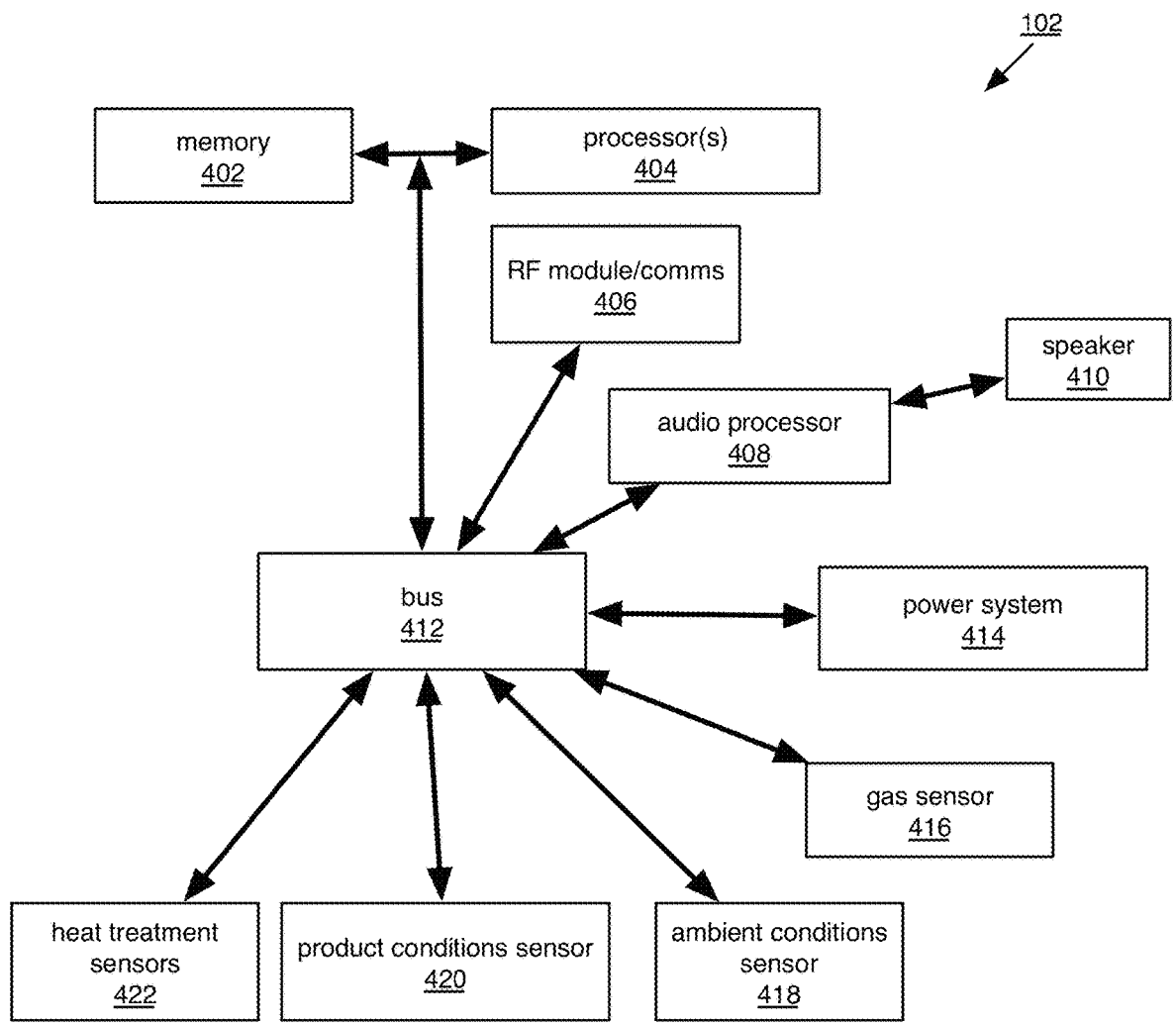
FIG. 4 shows exemplary components of an edge device in accordance with some embodiments of the invention.

FIG. 3 depicts an exploded view for an embodiment 300 of edge device 102. In embodiment 300, the cap 200 includes vents 206 arranged in two offset stacked rows, each row having approximately 15 beveled or countersunk openings. In certain embodiments, the vents are arranged into one, two, or three rows, and the openings are not beveled and bored perpendicularly to the surface of the cap. In embodiment 300, the cap 200 includes a first threaded portion (hidden in FIG. 3) that is complementary to the second threaded portion 303 of upper housing 202, such that cap 200 screws onto upper housing 202. The upper housing 202 includes a third threaded portion (hidden in FIG. 3), complementary to a fourth threaded portion 212 of lower housing 204. A magnetic ring 208 and switch suppress ring 210 encircle a portion of the fourth threaded portion 212, and when assembled, are located between the upper housing 202 and the un-threaded portion of the lower housing 204.

Figure 5:
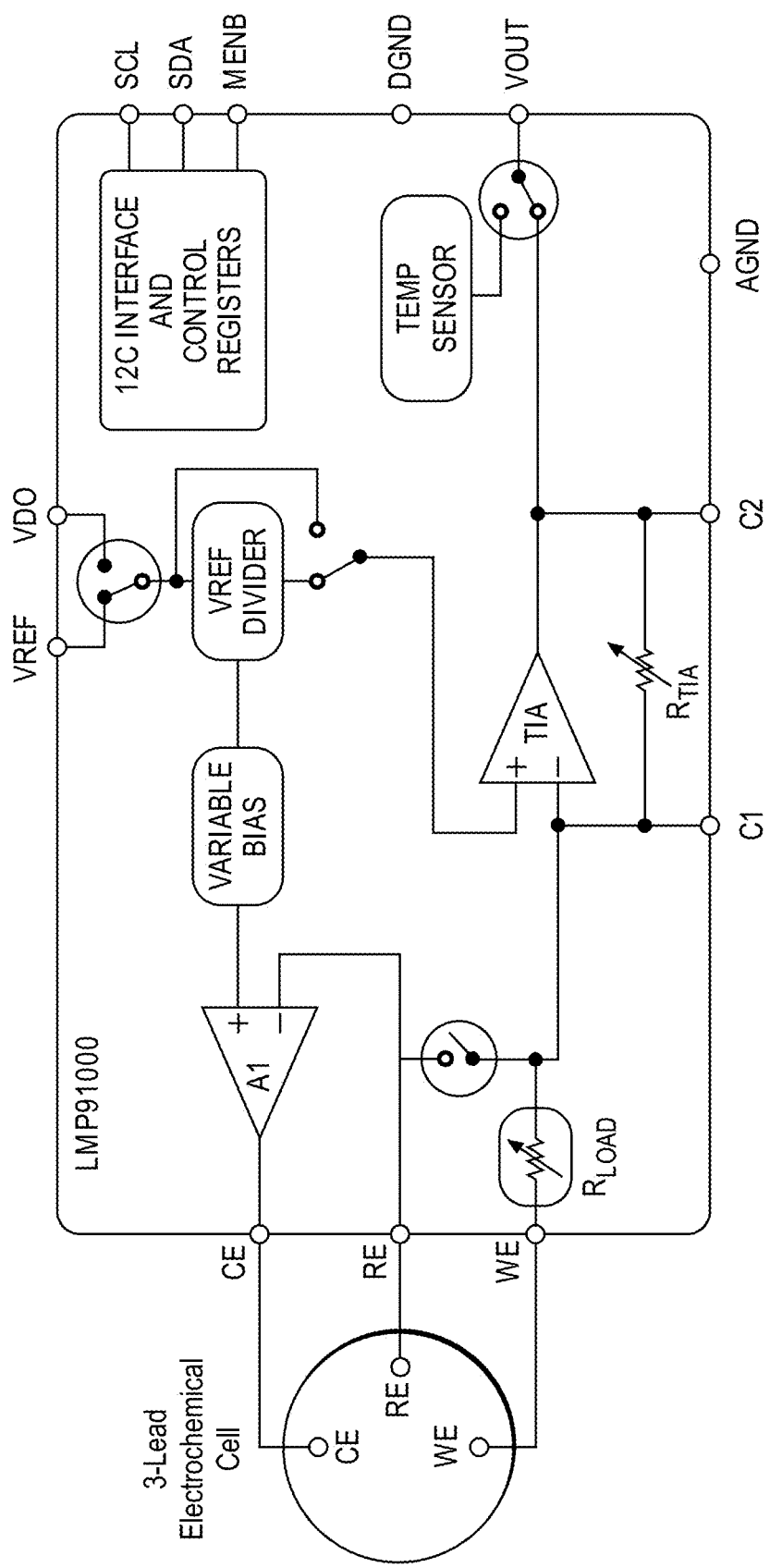
FIG. 5 depicts an exemplary sensor circuit diagram in accordance with some embodiments of the invention.

In embodiment 300, the upper housing 202 contains a sensor opening 305 in its upper face, through which an electrochemical gas sensor is exposed to air from the environment (e.g., air that has diffused in via vents 206 in cap 200). The electrochemical gas sensor comprises a sensor cell 306 and a sensor circuit board 308. In one embodiment, the sensor circuit board is designed around the Texas Instruments LMP91000 configurable AFE potentiostat for low-power chemical sensing. FIG. 5 is taken from the data sheet for this component and depicts a functional layout of the subject potentiostat coupled to an electrochemical gas sensor cell as may be used in an edge device 102 of a post-harvest crop management system 100. In this configuration, terminals SCL (clock), SDA (data), and MENB (module enable) define an I2C interface for interconnection with an appropriate microcontroller. In certain embodiments, a sensor circuit board 308 may use such a potentiostat to provide data from an electrochemical gas sensor cell to the main circuit board 324. In certain embodiments, the gas sensor may detect phosphine ($PH_3$), carbon dioxide ($CO_2$), ethylene, ammonia ($NH_3$), or ozone ($O_3$) by including the appropriate sensor cell and sensor circuit board. Phosphine detection may be useful for monitoring fumigation treatments, and carbon dioxide detection may be useful for detecting spoilage, in which increased concentrations of carbon dioxide may be indicative of the amount of spoilage. In certain embodiments, the same edge device 102 can be converted to sense a different gas by swapping the sensor cell 306 for an appropriate alternative sensor cell.

Embodiment 300 further includes a main board 324 on which various components are mounted. As shown in the illustrated example, one or more daughter boards, such as an antenna board 320 having an antenna 319 for wirelessly receiving and transmitting data from and to other edge nodes 102 and/or gateways 104, may also be electrically coupled to the main circuit board. In general, the main circuit board includes a Reed switch 322, a radio frequency (RF) transceiver 326 for modulating data to be transmitted via the antenna 319 and demodulating signals received via the antenna 319, and a buzzer 332 for generating alert noises and providing other audio feedback. As noted above, Reed switch 322 is an electrical switch that is actuated by bringing a magnet 336 (e.g., nickel-plated neodymium magnet) associated with (e.g., mounted on) the magnetic ring 208 in close proximity. Using a Reed switch allows activation/deactivation of the edge device without having to decouple the upper and lower housings from one another or the expense associated with air tight gaskets that would be needed if a toggle or other switch arrangement with components passing though the housing(s) were employed.

The components of the edge device are powered by a battery 330, and the main circuit board includes an appropriate connector 334 for interfacing with a battery power supply 330. In certain embodiments, the battery power supply 330 includes one or more lithium thionyl chloride battery cells, which provide the advantage of withstanding high heat, allowing the edge device to survive high storage temperatures or heat treatments. The main circuit board also includes a controller (e.g., a microprocessor or similar unit), which, in some embodiments is configured (e.g., via firmware stored in a non-volatile memory device) to cause the edge device to enter a low-power sleep state as appropriate for maximum operational life. One example of such a controller is a low-power microcontroller (MCU) processor, which supports the programming of applications and libraries which implement interconnection with peripheral devices, such as the sensors (e.g., an electrochemical gas sensor). Such peripherals, based on their specifications, may communicate with the MCU either through an analog port or through digital port using communication protocols, such as I2C, SPI, UART, serial, and the like.

The main circuit board also may provide appropriate wiring traces to interconnect the RF transceiver with the MCU, as well as various function indication lamps or LEDs, and other components of the edge device.

When assembled as shown in FIG. 3, the internal components of the edge device are maintained in separate internal compartments defined by seals provided by o-rings (e.g., upper rubber o-rings 302, small rubber o-rings 312). In this way, corrosive gasses from the environment being monitored will not come into contact with sensitive electrical components or the battery cells. The portions of the outer housing are screwed (or otherwise mounted) together, sealing the internal components within the inner, tubular space, and the housing pieces are secured through the use of a countersunk pin 304, which prevents the housing portions from coming loose. The internal components are maintained in the illustrated geometry using screws 318, various board-to-board interconnections 316, interface connectors 310, and screw stand-offs 314. In certain embodiments, components exposed to the external environment such as pin 304 and screws 318 may be formed from inox steel.

In certain embodiments, the edge device 102 is unique in enabling the use of electrochemical gas sensors (along with supporting electronics and wireless transmission) for in-situ placement in commodities and in the presence of corrosive fumigant gas, such as phosphine. Accordingly, a corrosive-chemical resistant housing with activation via a magnetic switch provide key functionality for such embodiments of the invention. Given that phosphine is a highly corrosive toxic gas, the housing of the edge devices has been designed according to the invention to protect all the vulnerable electronics from the penetration of gases. Accordingly, in certain embodiments, chemical-resistant o-rings of several diameters have been used in all the openings to seal the housing safely when it is closed. For example, two o-rings, 30 mm in diameter may be used to secure the sensor cell opening in the upper housing 202, and a third one (24 mm) may placed atop the sensor cell for extra sealing strength. In certain embodiments, 60 mm o-rings are used for the sealing of the main opening of the housing, through which the technicians can access the electronics and the battery pack. Moreover, the housing can provide a safety layer between the main board and the battery power source to protect the batteries from being in direct contact with the electronics board and/or being pierced, overheated or unstable. Embodiment 300 includes two upper rubber o-rings 302 placed between the cap 200 and upper housing 202 to create a seal between an environment-exposed compartment in the cap 200 and a sealed compartment within the upper and lower housing, four small rubber o-rings 312 to seal the screw holes for screws 318, and a lower rubber o-ring 338 to seal the interface between the upper and lower housing.

s. 4 shows exemplary components of an edge device 102. Device 102 may include one or more processors 404 (such as the MCU discussed above) that may be in communication with a storage component/memory 402, a communication module 406 (such as the RF transceiver 326), and a power system 414 (e.g., a battery power supply), via bus 412.

Device 102 may include various categories of peripheral sensors (e.g., 416, 418, 420, and 422). For example, edge device 102 may include one or more gas sensors 416, such as a sensor for detecting the concentration of $PH_3$, $CO_2$, or $O_2$ in air. Device 102 may include one or more ambient conditions sensor 418, such as a temperature sensor, solar radiation sensor, humidity sensor, wind sensor (speed, direction), and/or atmospheric pressure sensor. (In certain embodiments, ambient condition sensors 418 that provide measurements to system 100 are housed in an ambient condition device 103 that is not an edge device 102, e.g., for positioning and measuring environmental conditions outside of crop storage area 106, and that may not participate in the mesh network created by a collection of edge devices 102). Device 102 may include one or more product conditions sensor 420, such as a temperature or moisture content sensor. Device 102 may include one or more heat treatment sensor 422, such as a temperature sensor or thermal camera.

Device 102 may include an audio processor 408 and a speaker 410 for playing sound (e.g., for alerts, as an alternative to a buzzer 332). Communication module 406 may include a subscriber identify module (SIM) card, cellular radio, Bluetooth radio, ZigBee radio, Near Field Communication (NFC) radio, wireless local area network (WLAN) radio, GPS receiver, and antennas used by each for communicating data over various networks. Memory 402 may include one or more types of computer readable medium, such as RAM or flash memory, and may store an operating system, applications, communication procedures, and data generated by peripheral devices/sensors.

Edge Device Self-Test

A sensor testing procedure may be used to verify the connection and the functionality of the sensor in an edge device. One exemplary self-testing procedure using a sensor circuit board based on the TI LMP91000 shown in FIG. 5 comprises the following steps:

(1) I2C Interface connection check. I2C is a two-wire (SDA, SDCLK) interface, used to transfer serial data. In order to check the connection of these two wires between the main circuit board and the sensor circuit board, data is written to and read from an LMP91000 lock register. If the I2C interface connection is functional, the value that was written to the register will be properly read therefrom. Otherwise, an error is returned.

(2) Sensor Standard output check: In this step, the output of the sensor is checked in normal conditions (no presence of gas). At first, raw samples are taken for 150 seconds (1 sample per second), allowing the (new) sensor to settle. Then 20 samples are taken. The average of these samples is compared with predefined thresholds. These thresholds were set after testing 10 brand new sensors and 3 faulty sensors. Usually, a faulty sensor outputs a signal slightly higher than normal (0.52V instead of 0.48V). In such instances, an error message (e.g., "Faulty Sensor") is returned to the user. If the output is in rage of 1.5 V and above, there is also the possibility that the output female pin of the sensor circuit board is not properly connected to the male connector pin circuit board. In such instances, an error message (e.g., "Faulty sensor or bad connection to Vout") is returned. If the result exceeds the thresholds, an error message is returned. The gas sensor is connected to the analog front end (AFE) of the LMP91000. For communication with the AFE, the I2C interface is used.

(3) Pulse insertion: In the third and last step, a pulse signal is inserted in the Counter Electrode (CE) of the sensor. This is accomplished by inserting a bias voltage (1% of Vref). With this test, a verification that the sensor is successfully attached to the sensor board is made. For example: $R_{TIA}$ is changed to 7.5 k from the default of 35 k; bias polarity is changed to positive from the default of negative; bias is changed to 1% from its default of 0%; the bias polarity is restored back to negative; the bias is restored to 0%; and RTIA is restored to 35 k.

Antenna Design

The antenna must efficiently couple radio frequency energy between the outside environment and the internal package circuitry. In certain embodiments, the antenna 319 of the edge device is an electrically short inverted 'L' monopole with an orthogonal meander line top plate having a total line length of approximately a quarter wavelength. The monopole antenna functions against the solid printed circuit board ground plane counterpoise. The vertical radiation pattern is approximately uniform, similar to that for a full quarter wave vertical antenna, but has a non-uniform horizontal component that is useful for communications reliability in complex propagation environments, such as transmitting from inside bulk products (e.g., stored grain in a silo). The structure of such an antenna facilitates a considerable reduction in overall package height to that needed with a full size vertical radiator.

Figure 6:
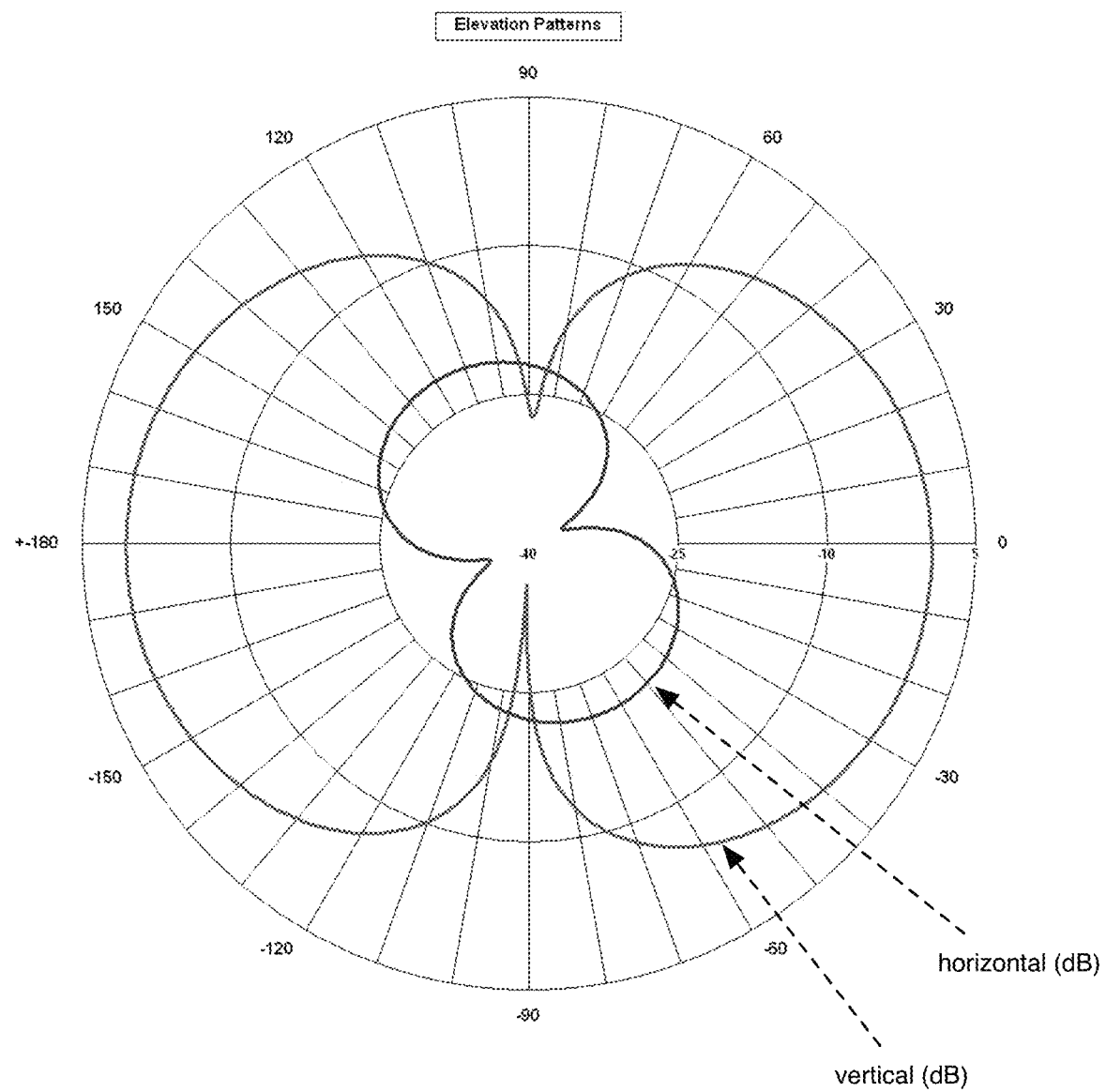
FIG. 6 depicts an antenna elevation radiation pattern for an exemplary edge device in accordance with some embodiments of the invention.
Figure 7:
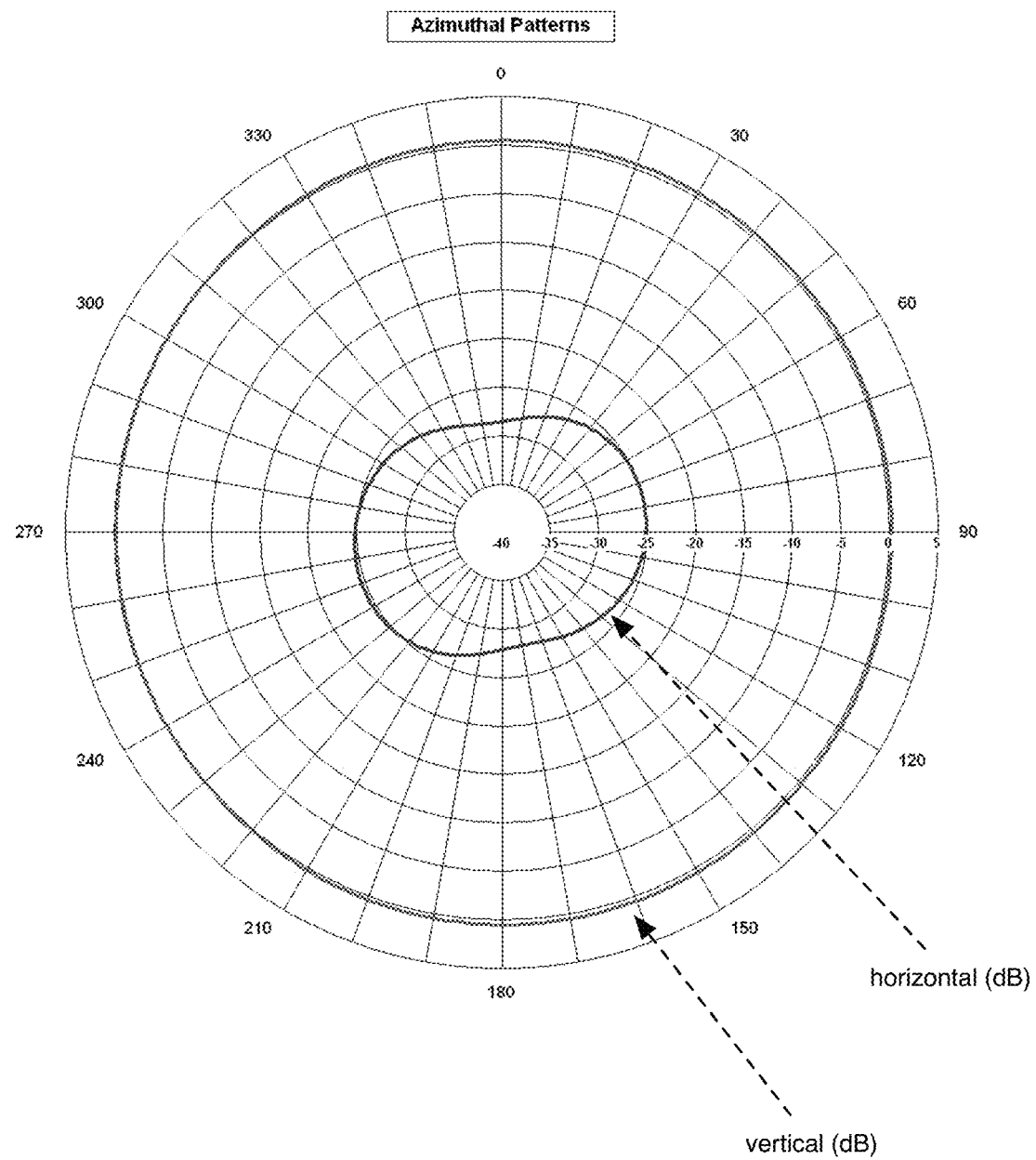
FIG. 7 depicts an antenna azimuthal radiation pattern for an exemplary edge device in accordance with some embodiments of the invention.

FIG. 6 shows elevation radiation patterns for antennas of edge device 102, and FIG. 7 shows azimuthal radiation patterns for antennas of edge device 102. Each figure shows radiation patterns for both horizontal and vertical polarizations. As shown in FIG. 7, the radiation pattern is omnidirectional in the azimuthal plane, which is desirable for the target environments, as any horizontally dispersed arrangement of edge devices throughout the crop storage area should maintain the communication flow within the mesh network. In certain embodiments, the antenna is tuned to frequencies such as sub-GHz unlicensed (ISM) bands, specifically the 865 MHz band for the EU/Africa and the 920 MHz for the Americas. Preferably, the antenna is tuned (by appropriate strapping of segments) to minimize losses such that no matching circuit is needed for connection with the wireless transceiver.

Network Design for Harsh Environments

In certain embodiments, the wirelessly transported sensor readings have to reach the gateway device 104 through thick obstacles, such as a high density of stored product. In addition, industrial facilities such as container yards, flour mills and logistics buildings usually cover large areas, which make the adoption of wireless communications very attractive. Achieving reliable wireless communications in such areas, though, is not a trivial issue. Furthermore, the industrial environment includes numerous metal constructions (post-harvest grains, dry nuts, tobacco and various other agriproducts which require pest treatment are often stored in metallic constructions, such as silos and containers) and sources of electromagnetic interference. Therefore, the edge devices 102 must communicate not only through obstacles, but also through metal, which creates an even more challenging situation. For these reasons, a set of assistive devices that will act as network repeaters may be required. In certain embodiments, edge devices 102 may be used as repeaters.

Battery-Powered and Always-On Repeaters

Edge devices 102 functioning as repeater devices aim to extend network coverage and facilitate message forwarding towards the network sink (e.g., the gateway 104). Depending on their installation, these repeaters may be battery-powered or "always-on" (i.e., supplied with main power). Both devices offer data forwarding to/from neighboring nodes or repeaters. In addition, repeaters not only convey data from their children-neighbors to the sink, but, in the case of battery-powered repeaters, also provide sleep period and clock synchronization messages to the children/neighbor nodes. That is, while always-on devices need not and do not "sleep" in a periodic manner to save energy, and therefore are able to serve any child-/neighbor-node within their network range even in the case of inter-device clock drifts, battery powered repeaters must synchronize their clocks with their child-/neighbor-node so that the child-/neighbor-nodes do not attempt transmissions while the repeater is asleep. In some networks, a communication protocol that makes use of sequential message numbers may be employed so that a repeater will recognize instances of missed messages from child-/neighbor-nodes. While it is usually not necessary to have such missed messages repeated (unless the message cycle time is very long or the environmental conditions being monitored are changing very rapidly), knowing that messages have been missed may be used as a prompt for the repeater to issue new synchronization messages to its child-/neighbor-nodes.

Device Calibration

Figure 8:
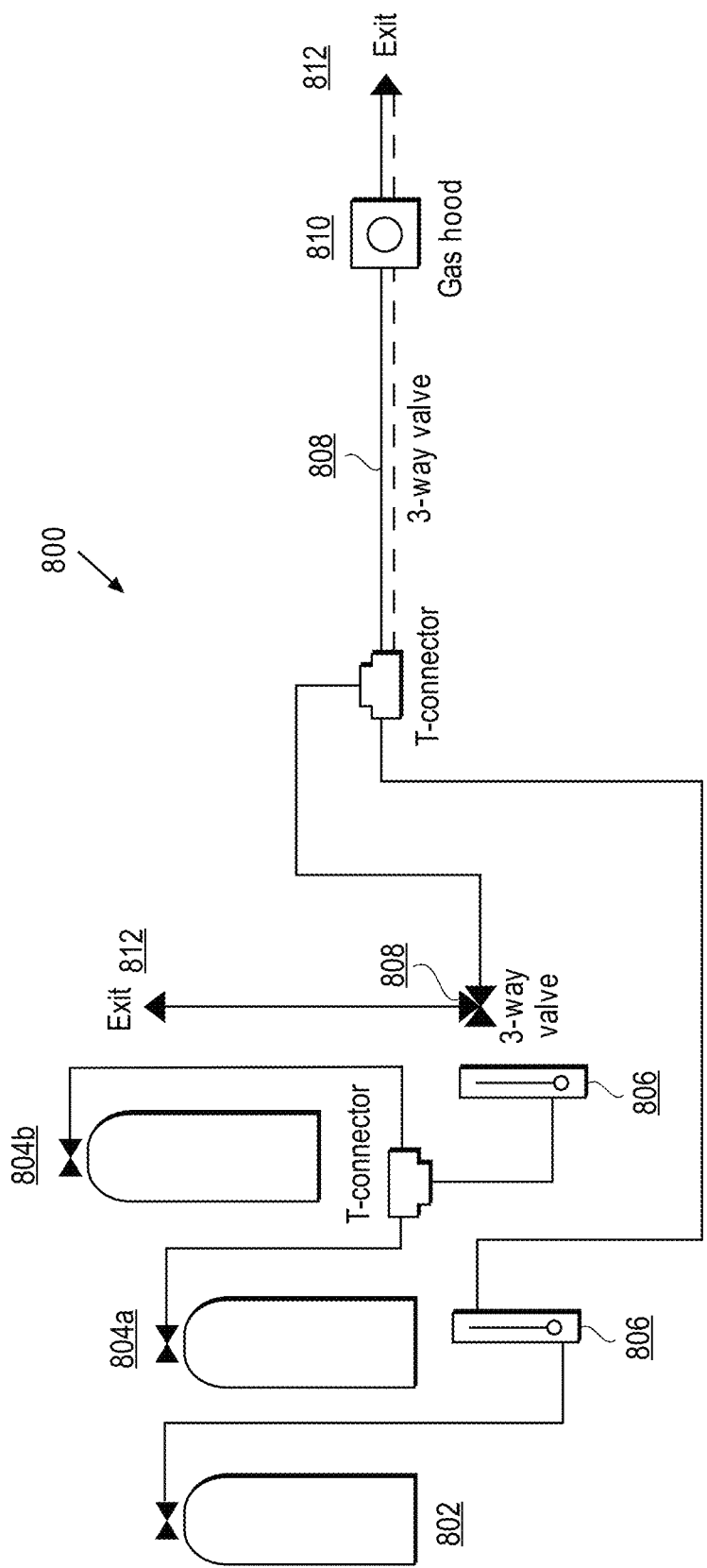
FIG. 8 depicts an exemplary calibration apparatus for an edge device in accordance with some embodiments of the invention.

It is desirable to ensure precision and agreement of readings among several edge devices 102. In certain embodiments, precision can be achieved via calibration against prototype gases of known concentration, for example where the edge devices include a gas sensor. Such a calibration process aims to optimize sensors' precision and evaluate their readings against reference gases to compensate for sensor aging after prolonged use and exposure to high fumigant concentration. The electrochemical cells (e.g., sensor cell 306) may operate in the amperometric mode based on several layers of electrodes over an electrolyte reservoir. Due to the fact that the electrolyte volume is finite, these sensors present aging over time. For the above-mentioned reasons a calibration setup has been designed. FIG. 8 depicts an exemplary fumigant sensing calibration apparatus 800 for an edge device 102. In certain embodiments, apparatus 800 uses chemical-resistant tubes connecting inox (stainless-steel) valves (e.g., three-way valve 808), connectors, and anti-corrosive Vernier valves 806 to exits 812 and a gas hood 810. In certain embodiments, the aim of this setup is to calibrate the sensors against 500 ppm and 1000 ppm $PH_3$ gases carried by nitrogen, or a proper surrogate gas such as $SO_2$. The apparatus 800 may include air tank 802, fumigant tank 804a having a lower known concentration of fumigant in nitrogen (e.g., 500 ppm phosphine), fumigant tank 804b having a higher known concentration of fumigant (e.g., 1,000 ppm phosphine).

In in certain embodiments, a calibration procedure using an apparatus such as 800 can be performed at the end user's location (e.g., at the location of the crop storage area 106), with the setup described herein implemented as a user-owned apparatus. When the device under calibration which is connected to the gas hood 810 is an edge-device 102 according to the invention, the calibration coefficients thus obtained can be stored in the cloud platform system disclosed herein (e.g., in remote data store 122, accessible via API 118), and/or in local data store 108. Thus it becomes possible to not only safely store the calibration coefficients in the cloud and conveniently recall them when the edge device 102 accesses the platform, but also to provide pre-emptive maintenance and data analytics tasks. For instance, the platform system can inform an end user when an edge device requires factory maintenance; the platform operator can perform quality control by aggregating calibration data for all the edge devices connecting to the platform, and thus improve the level of service it provides to end users; moreover, a cognitive system implemented in the cloud platform can provide increasingly more accurate correction factors, by being trained on the aggregate datasets produced when various end users perform calibration tasks on their edge devices.

Approaches for Managing Crop Quality

In certain embodiments, data are collected from an agriproduct or food storage facility via edge devices 102. The data are uploaded to a cloud server (e.g., server 116) or to the end user's own intranet (e.g., local data store 108 on a private network) or private cloud, where characteristics and plots can be viewed and analyzed from anywhere in real-time on smart devices equipped with the mobile app, and over the internet via PC, etc. (e.g., via user device 112). Thus, a large amount of data can efficiently be used in optimization of processes, e.g. to determine the exact duration of treatments such as fumigations, to issue alarm conditions and to predict time and conditions of successful treatments. The collected readings can be used to predict events and resolve or prevent potential quality issues, along with effecting productivity improvements based on historical and simulated data. Applying predictive models in real time means an end user can directly intervene early on in a long-lasting process, predict outcome and avoid failures.

Real-Time Data Monitoring

Real-time data arriving from edge devices 102 for stored crop quality monitoring may include multiple time series depending on the number of edge devices and respective sensors used, and may be used to create a graphical representation in chronological order. Data visualization is useful in order to present streaming data. As the sensor readings may be in time-series form, in certain embodiments, line charts are adequate since trends over time and alerting conditions on specific moments can be depicted.

Platform

Certain embodiments of the invention concern a service platform that may be a cloud-based application which provides all the necessary architecture elements for aggregating and presenting data, executing and presenting cognitive predictive and prescriptive analysis, interacting with third-party applications, and generating efficient interfaces for end-user interaction.

Architecture

The platform may be based on a microservice architecture. A microservice architecture restricts each service to a small set of responsibilities and provides it as a black-box component to be used or integrated with other microservices. This provides the advantages of easier testing, scaling and maintenance because each unit is only responsible for itself, and it only needs to comply with its published API definition or interface for integration.

In certain embodiments, the different microservices are built and orchestrated using the Docker Container Service (Docker, Inc.) which makes the system hardware & operating system-agnostic and easily portable with only a few configuration files enough to deploy the complete solution to a new location.

The platform may include these components: (1) Device Communication and data acquisition; (2) Main API—Authorization provider for the platform to be accessible; (3) Acquired Data Processing (real time rules, analytics, machine learning, etc.); (4) Web or mobile application as presentation layer.

Device Management

Sensor data (e.g., from sensors of edge devices 102) may provide raw material for the platform. This data is acquired from local sensor networks that are connected to the cloud through edge gateways (e.g., gateway 104). The edge gateway may run a fog-agent which is generally responsible for gathering the data from the local sensor network and sending them to cloud. The fog agent may also make sure the device is kept connected to the cloud, handle the device to cloud and vice versa communication, including device telemetry and device management commands. Finally, the fog agent may also provide the ability to change the configuration parameters for the local sensor network and provide remote access to the device (e.g., gateway 104 or edge devices 102).

Application Interface

In certain embodiments, an application interface (e.g., API 118) provides the entry point for the application (e.g., application 120) for any publicly available functionality. This can be used by a front-end web application as a data source, and also as an API for any interested consumer. It also implements authentication and authorization for accessing different resources based on roles to create different levels of access for each user.

Data Processing

Data processing concerns the manipulation of raw data (sensor, weather, etc.) after the collection of them. Data may arrive in real time, or in a batch after edge device was offline, from connected edge devices, or services generating data (such as weather recording and quality metrics for each process). Upon data receipt the data may be streamlined to different consumers whose operation is independent from each other.

Storage

The most basic functionality is to store the data in persistent storage (e.g., NoSQL database, involving remote data store 122) to be available for further processing. The data is aggregated in an optimal manner for the application, in order to be more efficient in storage size and access—retrieval performance. In this way the readings are available for any process that requires historical data.

Recipes

Incoming edge device data may be passed through a recipe rule engine and for each rule that is validated, a predefined action occurs. Recipes comprise rules. Rules may be sets of user defined conditions, concerning the values of device telemetry. The advantages of this invention compared to the other available rule engines include:

(1) Support stateful conditions. Most systems provide logic that can only be applied on the actual isolated payload of the device, and have mostly to do with simple value operators (greater than, equal, and the like). In certain embodiments, the platform provides the ability for each condition to store a state as well as take into account historic data, for evaluating its result.

(2) Support for multiple simultaneous conditions. When a required logic is too complicated to be evaluated in a single condition, embodiments of the platform may provide the ability to define a set of multiple conditions that must be fulfilled in order for the rule to be considered valid.

(3) Support for rule prerequisites. In case a rule is relied upon for validation of a separate rule, this can be added as a prerequisite for the former, so that it will only validate when the prerequisite rule validates.

For each rule or recipe, when the conditions are valid a set of predefined actions can occur. These include sending an email, in-app notifications, and the like.

Analytics

The platform includes an analytics system. The ability to process raw metrics and provide helpful insights to the customer is what it matters the most for the end user. Certain mechanisms provide intelligence on different aspects and usage scenarios:

Heat treatment predictive analytics, where valuable info is given based on historic data of previous heat treatments allowing the end user to make quick decisions for the treatment.

Optimal $PH_3$ dosage recommendation, for optimal results in a $PH_3$ fumigation process.

Calculation of $PH_3$ concentration over time inside asset, for an estimation and overview of the fumigation process to take place in an asset.

Estimated time at completion of successful fumigation, based on the actual recorded state of the running process and its compliance with proper procedures.

Safe storage time of stored product, to give the end user the ability to plan accordingly his/her actions having the estimate of product safe dates.

The analytics system may function in a complete asynchronous and non-blocking manner. A basic workflow may include: (1) Analytics Service receives a task to be executed; (2) Different types of workers run specific job types as assigned to them; (3) After the work is done, the main application is signaled with the result.

Presentation Layer

In certain embodiments, the application is cloud based, cross-browser compatible and its layout is mobile responsive. Web socket communication is a key characteristic of the application as it depends on real time notifications and data feed.

In certain embodiments, in the application, the user has the ability to monitor the devices he/she owns and to view general information and historical data of all the entities. In certain embodiments, the main structure consists of five main entities, the Activities, the Processes, the Recipes, the Assets, and the Devices. Each entity has its own properties and functionality that help the user to monitor, organize and visualize the provided measurements, incoming from multiple sources.

Devices

The device section contains the user's acquired hardware. It includes two subsets, the gateways 104 and the edge devices 102. The gateways are devices that collect the measurements by sensors of the edge devices. The gateway section may display an overview of real time sensor readings as well as general information about the location of the devices, communication statistics and hardware configuration. The location of the devices may be a geographic location (e.g., a city name, a zip code, or GPS coordinates) or an internally named location (e.g., "facility 285"). The sensor section may contain specific sensor information such as notes, unique id and custom names concerning edge devices.

Assets

The Asset section refers to the users' actual properties, like buildings, storages, warehouses or any other entity at which the user will place edge devices (i.e., crop storage area 106). In certain embodiments, the user has the functionality to input and store key characteristics of the asset. More specifically, the user can input the type of the asset (warehouse, storage, etc.) its dimensions, its geographic location and the type and quantity of the product (crop) stored in it (if any).

Furthermore, in certain embodiments, the user may draw the main area of the asset, with the help of a drawing tool, in order to assign the specific sensors' locations. The sensor/edge device location within the asset may be defined using three-dimensional spatial coordinates relative to an origin point. This section may also provide information regarding the treatments that currently take (or took) place at it and the condition of the contained stored product based on calculated Quality Control Metrics (see description of Quality Plan below).

Recipes

In certain embodiments, the Recipe section contains functionality that allows the user to define conditions regarding the measurements and notify the user through various channels (in-app notifications, emails, and the like) when these conditions are fulfilled. Conditions may concern the status of an asset or the crops within it, as determined using an analysis approach provided by the platform. For example, a recipe may be used to define a notification responsive to changes in the estimated time of completion of a particular type of treatment in a particular asset. These recipes can be assigned and reused in multiple edge device groups or to a single edge device.

Activities

In certain embodiments, the Activity section has two main subsets, the Treatment Plan and the Quality Plan. The Treatment Plan section guides through the user to define various parameters such as the type of the treatment (Fumigation, Heat Treatment etc.), the items that the user wants to fumigate and their environmental conditions. These parameters may be used as for calculation of an approximately estimated time to completion for the heat treatment or fumigation. The Quality Plan section may prompt the user to enter the environmental conditions of their product stored in an asset and as result it returns to the user, metrics and statistics that help the user monitor the quality of that product over time.

Processes

In certain embodiments, the Process section provides the user the ability to monitor sensor measurements or various metrics for a specific time span. In certain embodiments, each process can monitor one or multiple gateways, specific sensors, quality control metrics or weather condition readings. The measurements can be displayed in real time in tiles or in graph view. Moreover, the user may be able to place the edge devices as items in the Asset drawing and monitor their measurements.

Figure 9B:
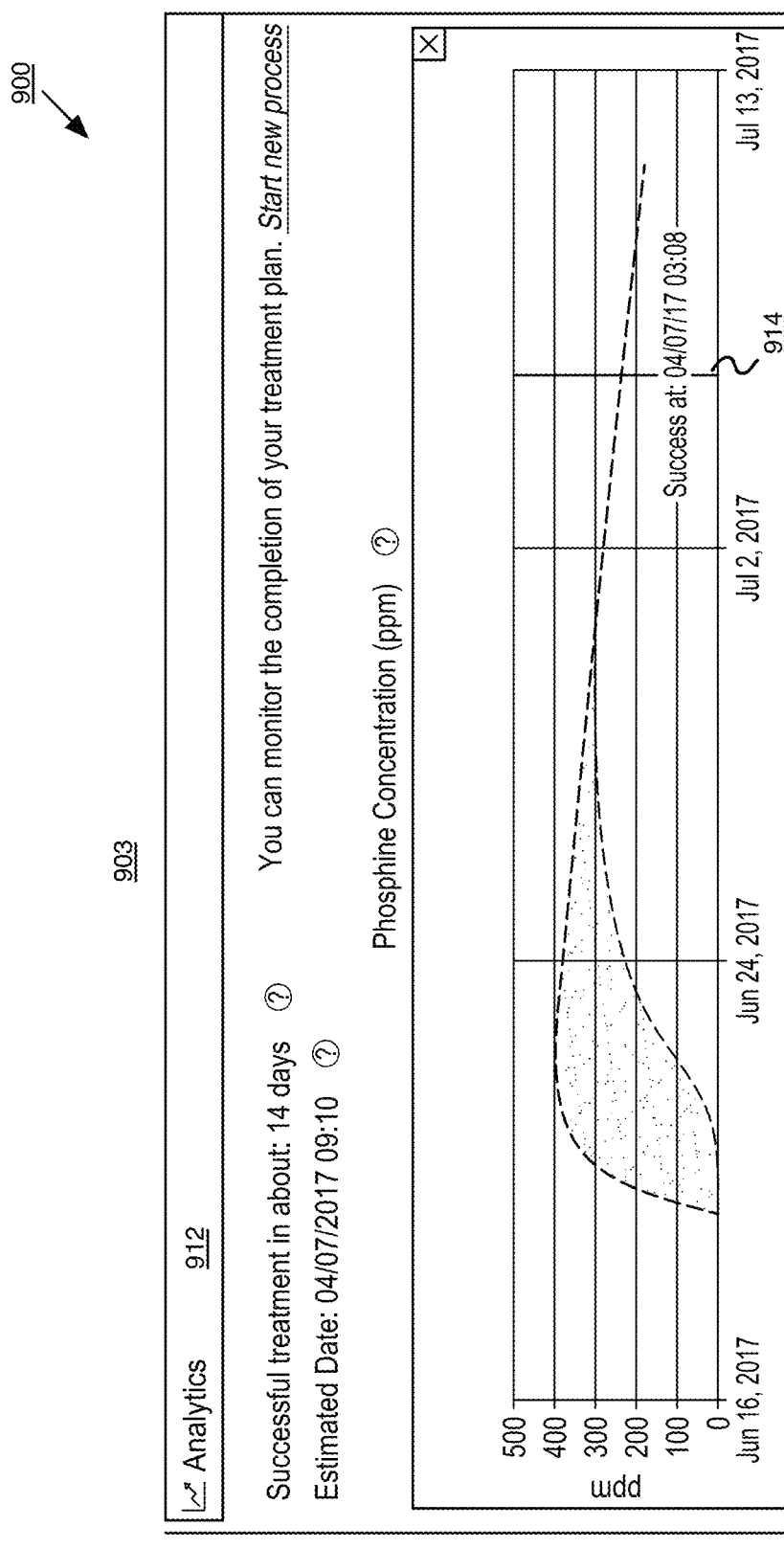

FIG. 9A and FIG. 9B show an exemplary embodiment of post-harvest crop management user interface (UI) 900, e.g. for a user device 112. UI 900 permits viewing and configuring a Treatment Plan. FIG. 9A shows a navigation panel 902, allowing the user to navigate between UIs for a dashboard, activities, processes, recipes, assets, devices, and settings. Editor panel 902 presents options for editing a treatment plan. For example, treatment type options 904 permit selecting a type of treatment (e.g., phosphine fumigation). Asset options 906 permit editing properties of the asset, such as its type, fill percentage, location, volume/dimensions, and type of stored product (e.g., whole wheat). Pest type options 908 permit selecting one or more pests that may affect the product. Treatment options 910 allow selection and calculation of a recommended treatment dosage. FIG. 9B shows analytics panel 912 within editor panel 903. Analytics panel 912 may present a determination of the expected treatment duration and a chart view of the expected course of treatment. For example, as shown in FIG. 9B, for a phosphine treatment associated with the user-selected parameters shown in FIG. 9A, analytics panel 912 presents the expected range of phosphine concentration within the asset in a chart view across a period of days of treatment, including a completion indicator 914 to indicate the time at which the treatment is expected to be complete. In certain embodiments, the treatment is expected to be complete at the time when less than 1% of the identified pests are expected to have survived the fumigation.

Figure 10B:
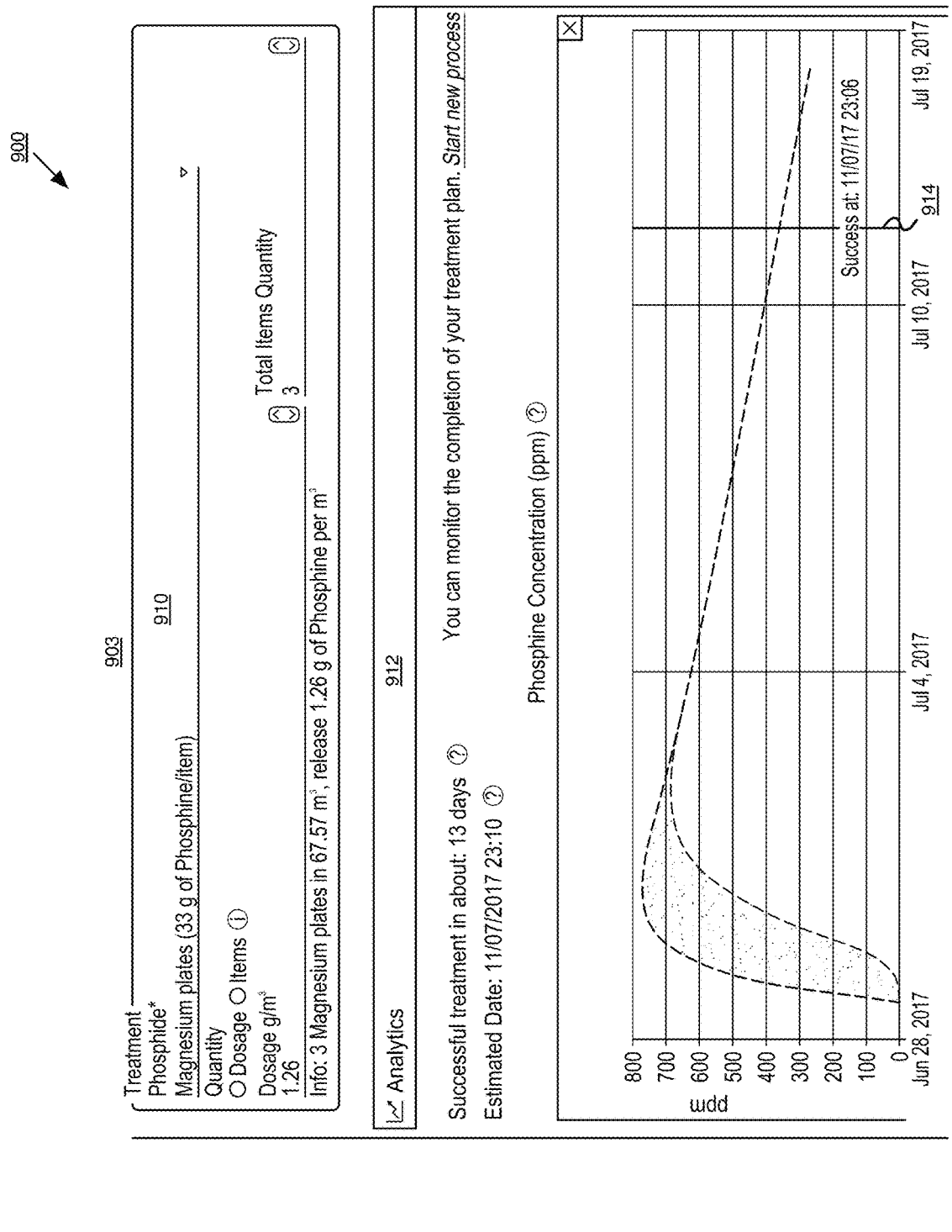

FIG. 10A and FIG. 10B show an exemplary embodiment of post-harvest crop management user interface 900, configured with different user-selected options relative to FIG. 9A and FIG. 9B. Additionally, FIG. 10A shows product conditions options 1002 within editor panel 903, by which data sources for temperature and relative humidity can be set, as well as expected leakage of the asset. For example, selecting the "weather" option may cause the temperature or humidity to be set according to a third-party weather information service such as weather.com or darksky.net using the provided location of the asset, selecting "sensor" will source the temperature or humidity using sensors of one or more edge devices 102 within the asset or an ambient condition device 103, and selecting "manual" allows the user to directly input the temperature or humidity. FIG. 10B shows, in analytics panel 912, a determination of the expected duration for a phosphine treatment based in part on the temperature and humidity defined via product conditions options 1002.

Figure 11A:
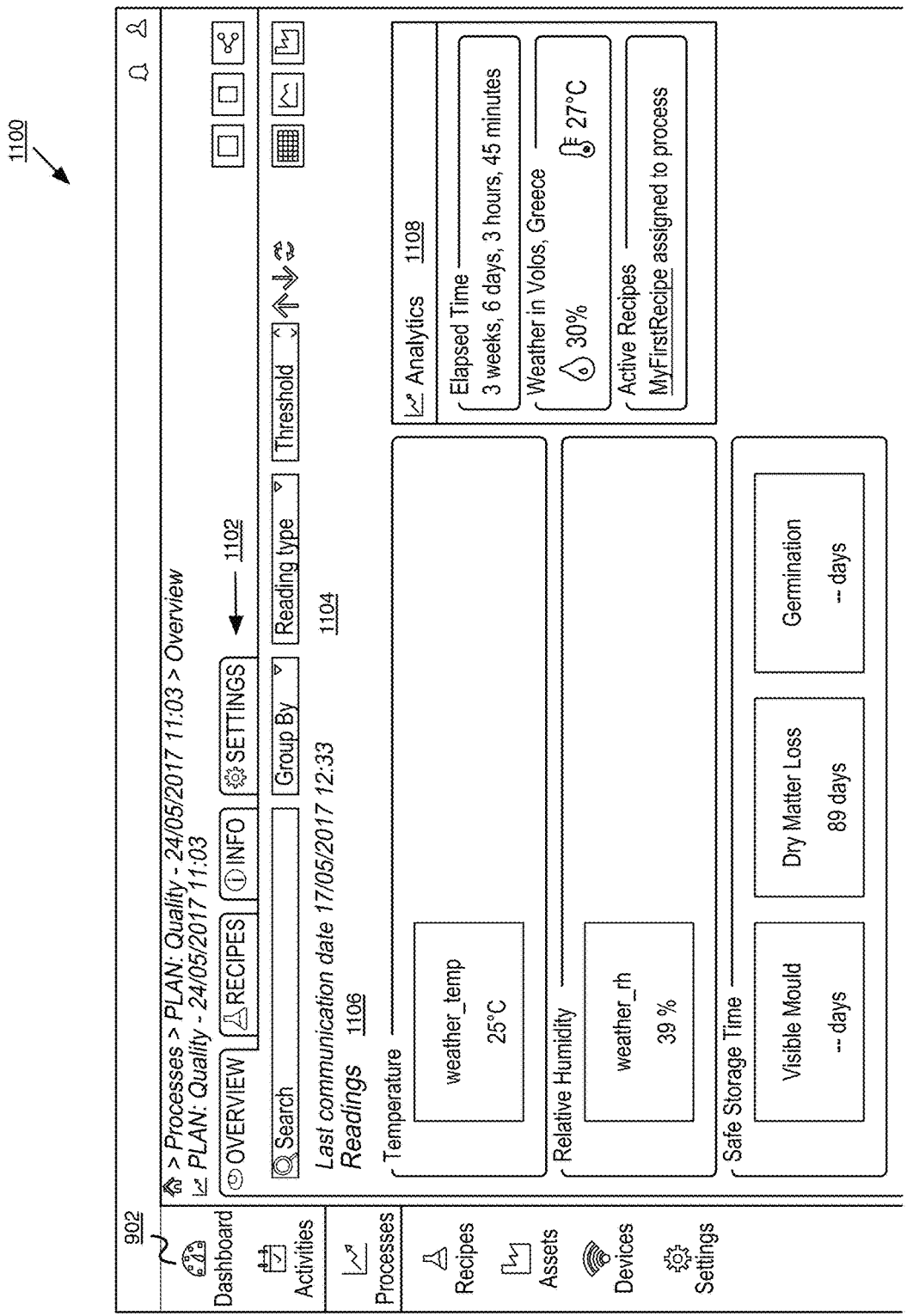
FIG. 11A and FIG. 11B show an exemplary post-harvest crop management user interface in accordance with some embodiments of the invention.
Figure 11B:
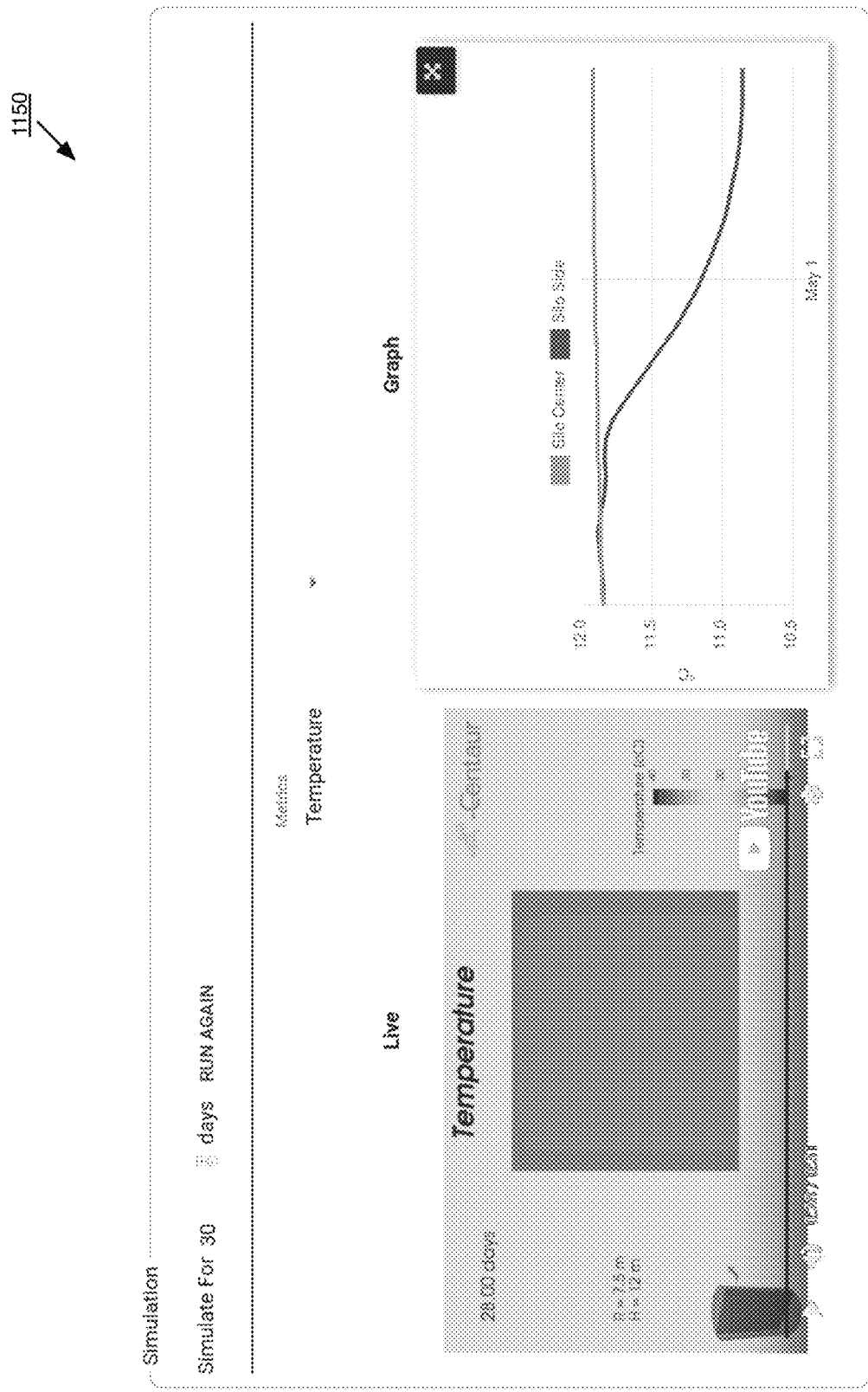

FIG. 11A and FIG. 11B show an exemplary post-harvest crop management user interfaces 1100 and 1150, e.g. for a user device 112. UI 1100 permits viewing and configuring a Process as part of a Quality Plan. UI 1100 includes process navigation tabs 1102 for navigating between an overview, recipes, information, and settings. UI 1100 additionally includes a content panel 1104 containing a readings listing 1106 and a process analytics panel 1108. Readings listing 1106 may provide a real-time listing of environmental conditions of the stored product (e.g., weather related measurements such as temperature and relative humidity). In certain embodiments, the readings listing 1106 may present information about an expected safe storage time with respect to an expected number of days until the product will evidence visible mold, dry matter loss, and/or germination. Such predictions may be based on the measured environmental conditions. The patterns, in the entire silo storage, of the above parameters, may also be presented in videos or time series graphs as shown in UI 1150 of FIG. 11B.

Computational Fluid Dynamics

In phosphine fumigations, it is important to ensure that phosphine concentration exceeds the predefined ppm levels in the entire storage space, e.g., to ensure insect mortality of 99.9%. In order to increase the spatial resolution of sensor data, Computational Fluid Dynamics (CFD) models are used. CFD is a branch of fluid mechanics that uses numerical analysis and data structures to solve and analyze problems that involve fluid flows. Computers configured to perform the calculations required to simulate the interaction of liquids and gases with surfaces defined by boundary conditions. In this invention, a CFD model is developed specifically to meet the parameters involved in fumigations. Among others, results may include phosphine concentration profiles for every location (both empty and filled with grain regions), temperature, and air velocity in time. Alternatively or in addition to phosphine, gasses important for stored product condition such as carbon dioxide, ethylene, ammonia, or ozone may be simulated in models like those described below.

Figure 12:
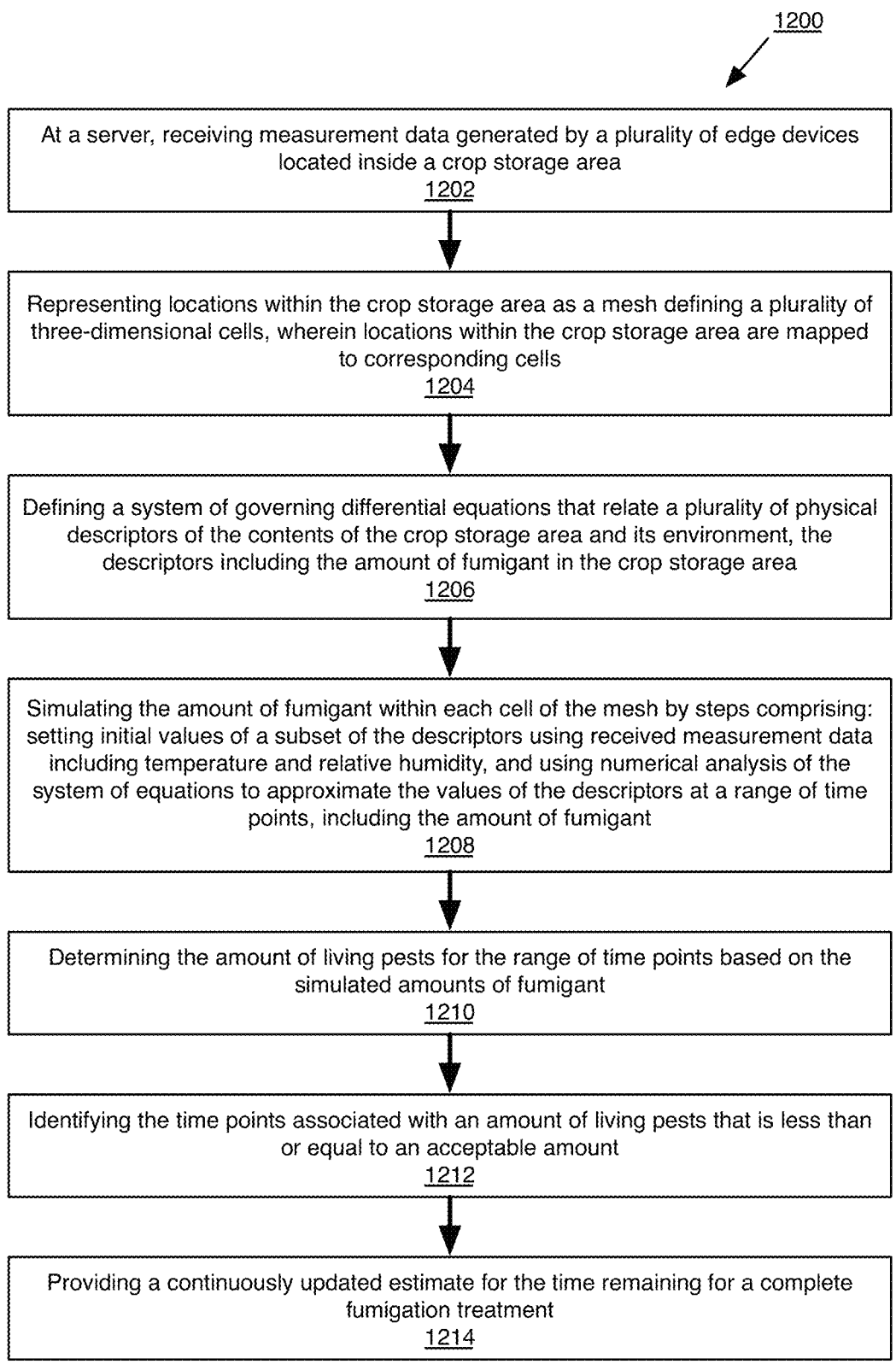
FIG. 12 shows a flow chart for an exemplary process concerning determining the duration of a fumigation in accordance with some embodiments of the invention.

FIG. 12 shows a flow chart for an exemplary process 1200 concerning determining the duration of a fumigation. To begin, a server (e.g., server 116) receives measurement data generated by a plurality of edge devices 102, where the edge devices may be positioned in various locations within a crop storage area 106 (1202). (In certain embodiments, an alternate version of step 1202 and process 1200 may be performed at a computing device that is geographically local to the crop storage area 106.) Edge devices 102 may be conveniently positioned, or may be evenly spaced throughout the crop storage area—for example, the edge devices may be positioned so that they are separated by about 1, 5, 10, or 20 meters across the floor or separated within a horizontal (x-y) or vertical (y-z) plane of the crop storage area. In certain embodiments, the received measurement data may be, for example, generated by one or more peripheral sensors such as a gas sensor 416, an ambient conditions sensor 418, a product conditions sensor 420, or a heat treatment sensor 422. The measurement data may concern the local physical environment for the corresponding edge device that generated the respective measurement—for example, an individual measurement of the measurement data may be a measurement of temperature, gas/fumigant concentration, or moisture content for a particular edge device (and, e.g., associated with the physical location of the edge device within the crop storage area via an identifier for the edge device), as well as the specific type of measurement such as "$PH_3$" and/or the category of the type of measurement such as "fumigant concentration"), and the date/time at which the measurement was taken by the sensor of the edge device. Edge device measurements of, e.g., fumigant concentration, temperature, moisture content, and/or relative humidity correspond to the medium measured at the location of the respective edge device, and thus characterize the air and/or crop at the location. In certain embodiments, the server may additionally receive data from a source that is not an edge device 102, such as a third-party service providing geographic weather information for the city hosting the crop storage area, or a different type of device having an ambient conditions sensor 418.

Locations within the crop storage area may be represented as a mesh defining a plurality of three-dimensional cells, such that the physical locations in the crop storage area are mapped to corresponding cells of the mesh (1204). For example, each coordinate position within the crop storage area (e.g., a physical location) will have a corresponding position in the coordinate system of the mesh. In certain embodiments, each cell is the same size and shape. In certain embodiments, certain categories of cells provide a higher resolution representation of the corresponding regions in the crop storage area 106 compared to lower resolution representations (e.g., higher resolution representations of a region are associated with larger numbers of smaller cells).

A system of governing differential equations may be defined to relate a plurality of physical descriptors of the contents of the crop storage area and the environment of the crop storage area, wherein the descriptors include the amount of fumigant in the crop storage area (1206). As used herein, "physical descriptors" are quantitative physical parameters that describe the materials within and at the boundaries of the crop storage area and their properties of interest, such as the concentration, sorption rate, temperature, and velocity of a fumigant gas at a position at a time. The physical descriptors may determined by, for example, transport equations for modeling incompressible fluid flow, heat, and mass transfer of a gas (e.g., where the gas may be a fumigant), taking into account temperature and pressure; porous medium effects, where the medium is the stored product (crops); a medium tortuosity effect on diffusion; the effect of sorption of one or more gases by a medium; gas release rate from a dispenser such as a tablet or sachet; and oxidative degradation of the gas. The environment of the crop storage area may be represented using boundary conditions—e.g., mass convective boundary conditions and thermal convective boundary conditions. Such a model according to the invention has not been previously reported using a three-dimensional mesh and associated equations adapted for three dimensions, and avoids the need to assume symmetry in the third dimension, an assumption that is not valid for most storage facilities.

The amount of fumigant may be simulated within each cell of the mesh by, for example, setting the initial values of a subset of the physical descriptors using the received measurement data, including the temperature and relative humidity, and using numerical analysis of the system of governing differential equations to approximate the values of the physical descriptors at a range of time points, including approximating the value of the amount of fumigant (1208). For example, the initial values of physical descriptors may be set using edge device 102 measurements of temperature and/or relative humidity. In such an example, the actual measured value of the physical descriptor may be used for the initial value of the corresponding location/position in the mesh, and initial values for intermediate locations may be extrapolated based on an average of surrounding edge device position measurements. Numerical approximations of the solution(s) to the system of governing differential equations may be obtained using a CFD solver. Accordingly, the system may be simulated to approximate its behavior throughout the mesh/crop storage area at later time points, including approximating the fumigant concentration profile for the crop storage area at later time points.

The amount of living invertebrate pests (i.e., undesirable insects, arachnids, nematodes, and gastropods), and their pre-adult stages (e.g. eggs, larvae, pupae) may be determined for the range of time points based on the simulated amounts of fumigant (1210). The time points associated with an amount of living pests that is less than or equal to an acceptable amount may be identified (1212). More specifically, the effect of a fumigant on the mortality of invertebrate pests is based on the level of fumigant concentration and the duration of exposure. The fumigant concentration profiles determined in step 1208 may be used to determine whether, at a particular time point, there may be any live pests remaining in the crop storage area. For example, the simulation may determine a portion of the mesh may be associated with a relatively low concentration of fumigant two hours after commencing a fumigation with a particular dose of fumigant. Even if other portions of the mesh would represent portions of the crop storage area in which the pests have been exposed to a sufficiently high concentration of fumigant for a sufficient period of time, this example would indicate that a higher dose or longer fumigation is necessary to effectively fumigate the storage area. In certain embodiments, the acceptable amount of living pests may be zero, an amount of pests that is too low to be measured, or less than 1% of the pests remaining alive.

A continuously or periodically updated estimate for the time remaining for a complete fumigation may be reported, e.g., to a client device such as user device 112 (1214). The time remaining may be, for example, the estimated date and time until the acceptable amount of living invertebrates will be achieved (i.e., the time when the fumigation will be complete). In certain embodiments, the positions with worst-case (lowest) fumigant levels are reported. Such information may be useful to identify an optimal location for placing a fumigant dispenser, or to identify an optimal location for placing an edge device in order to monitor the most challenging-to-fumigate locations inside the crop storage area.

In certain embodiments, the edge devices are used to measure the actual concentration of a fumigant, and regions of discrepancies between actual and simulated concentrations of fumigant are used to troubleshoot the fumigation. For example, additional fumigant dispensers may be added to areas with low fumigant concentrations, air recirculation systems may be switched on or off, or the discrepancy may indicate leakage of fumigant from the crop storage area.

Figure 18:
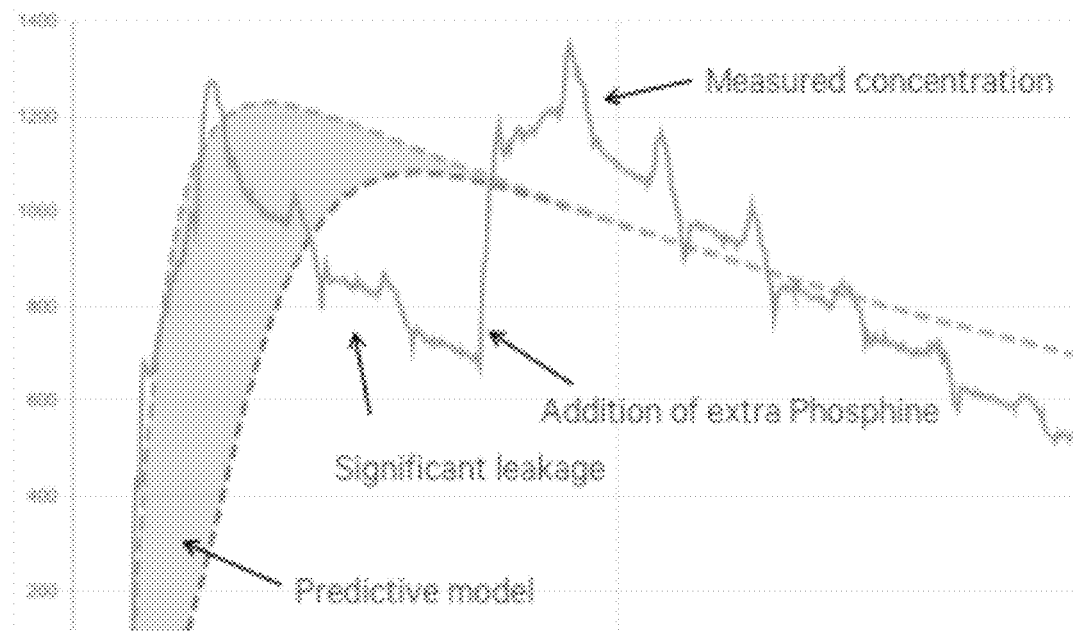
FIG. 18 shows an exemplary fumigation treatment course exhibiting fumigant leakage in accordance with some embodiments of the invention.

In fumigation treatments, weather data (e.g., temperature, pressure, relative humidity, solar radiation, and wind measurements) may be used to evaluate the degassing rate of phosphine, to calculate accurate values of the thermodynamic and transport properties of air at atmospheric pressure (air properties) and to properly parameterize the thermal convective boundary conditions. Based on the resulting model, the expected phosphine concentration may be approximated for the crop storage area. If the edge device sensor readings are below the predicted values, this may be a sign of significant leakage. Accordingly, additional fumigant should be placed in the storage. FIG. 18 shows an exemplary fumigation treatment course exhibiting fumigant leakage. In FIG. 18, the predicted average concentration of phosphine is shown overlaid with the actual measured concentration from a single edge device.

\* \* \*

EXAMPLE 1

A CFD Model for Estimating Phosphine Concentrations

Example 1.1

Governing Transport Equations

The CFD solver may be implemented using OpenFoam v.3.0.1 (OpenFOAM Foundation, Ltd.) in order to solve the following transport equations for incompressible fluid flow, heat and mass transfer, accounting for porous media effects:

$$\nabla u = 0 \quad (1)$$

$$\frac{\partial u}{\partial t} + \frac{1}{\phi} u \nabla u = \quad (2)$$

$$-\phi \nabla p + \nu \nabla^2 u - \phi \frac{\nu}{K} u - \phi \frac{F_e}{\sqrt{K}} |u| u + \phi g \beta (T - T_{ref}) + \phi g \beta_c (C - C_{ref})$$

$$\frac{\partial T}{\partial t} + \phi \frac{(\rho C_p)_f}{(\rho C_p)_{eff}} u \nabla T = \frac{k_{eff}}{(\rho C_p)_{eff}} \nabla^2 T \quad (3)$$

$$\phi \frac{\partial C}{\partial t} + \phi u \nabla C = \phi \nabla^2 \left(\frac{D_m}{\tau} C\right) - \phi B_1 C + B_2 q \quad (4)$$

$$\frac{\partial q}{\partial t} = -B_3 q + \phi B_4 C \quad (5)$$

In the above equations (1)-(5), u is the velocity vector, and p, T, and C are the pressure, temperature, and gas concentration in air, respectively. $D_m$ is the binary diffusion coefficient [m$^2$ s$^{-1}$]. Buoyancy forces created by both temperature and concentration gradients are considered in the momentum equations using the Boussinesq approximation. Under the Boussinesq approximation the variation of density $\rho$ with temperature T is linear, according to $\rho = \rho_{ref} - \rho_{ref} \beta (T - T_{ref})$. The volumetric coefficient of thermal expansion $\beta$ is given by $$\beta = -\frac{1}{\rho}\left(\frac{\partial \rho}{\partial T}\right)_p = \frac{1}{T}$$

for ideal gases
and the species expansion coefficient $\beta_c$ is given by $$\beta_c = -\frac{1}{\rho}\left(\frac{\partial \rho}{\partial C}\right)_p = \frac{1}{\rho_{air}}\left(\frac{MW_{air}}{MW_{gas}} - 1\right)$$

for ideal gases
where $MW_{air}$ and $MW_{gas}$ are the molecular weights of air and dispersed gas (e.g. phosphine), respectively.

Example 1.2

Porous Media

In order to account the effect of grains to the fluid flow, the grains are assumed to be a porous medium. Flow in porous layers is described by the Darcy-Brinkman formulation. The geometric function $F_e$ and the permeability K of the porous medium are related to the porosity $\phi$ based on Ergun's experimental investigations:

$$F_e = \frac{1.75}{\sqrt{150 \phi^3}} \quad (6)$$

$$K = \frac{\phi^3 d_p^2}{150(1-\phi)^2} \quad (7)$$

The effective properties $(\rho C_p)_{eff}$ and $k_{eff}$ are calculated as a function of the fluid and porous material:

$$(\rho C_p)_{eff} = (1-\phi)(\rho C_p)_{solid} + \phi (\rho C_p)_f \quad (8)$$

$$k_{eff} = (1-\phi) k_{solid} + \phi k_f \quad (9)$$

The above formulation is valid when thermal equilibrium exists between the fluid and the porous medium. Soret effect (mass flux produced by a temperature gradient) and Dufour effect (heat flux produced by a concentration gradient) are considered negligible.

OpenFOAM offers the flexibility of modeling incompressible flow through porous medium, using the explicit-PorositySource feature of the fvOptions, which adds the Darcy-Forchheimer source terms (Eqs. 6 and 7) in the momentum equation (Eq. 2). In OpenFoam notation the Darcy-Forchheimer equation is described as:

$$S_i = -\nu d u - 1/2 f |u| u \quad (10)$$

Correlating the above equation with Eqs. 6 and 7, d and f coefficients could be calculated as:

$$d = \phi \frac{1}{K} \quad (11)$$

$$f = \phi \frac{2F_e}{\sqrt{k}}$$

The implementation of porosity term in the momentum equation is necessary in order to produce results with high levels of accuracy.

Example 1.2.1

Tortuosity

Consider a scenario where the species only diffuse within a constant density fluid in a homogeneous porous medium without a source or sink. In this case, the solution of mass transport equation does not depend on porosity since diffusion time and length scales are not functions of the porosity. This implies that the concentrations will be identical when the user stipulates 0% or 100% porosity, an incorrect result. To represent the role of porosity on ordinary molecular diffusion, the diffusion coefficient in Eq. 4 must be scaled with tortuosity (Shen and Chen, 2007)). Tortuosity is defined as the ratio of the length of the curve to the distance between the ends of it. There are two approaches in the literature involving tortuosity on the effective diffusivity coefficient:

$$D_{eff} = \frac{D_m}{\tau} \quad (12)$$

$$D_{eff} = \frac{D_m}{\tau^2} \quad (13)$$

The first (Eq. 12) is proposed by He et al. (2014) and is also the one used for the present OpenFoam solver. The second approach (Eq. 13) is proposed by (Shen and Chen, 2007). In their study, Neethirajan et al. (2008) calculated $\tau=2.4$ for wheat and Ahmdad et al. (2012) measured $\tau$ between 38 and 275 depending on water-cement ratio, cement content and coarse-fine aggregate ratio.

Example 1.3

Sorption

Phosphine is adsorbed by grain at differing rates depending on the grain type. Sorption can reduce the concentrations of fumigation doses to sublethal levels before grain has been disinfested. A model to predict fumigant losses due to sorption is considered necessary. Researchers (Darby, 2008) have suggested that the relationship between the fumigant concentration in the interstices between the grain, C, and the average concentration of fumigant within the grain kernel q, is modelled by Eqs 4 and 5 which assert that phosphine is absorbed into the grain and at the same time also degrades in air. The coefficients $B_1$, $B_2$, $B_3$ and $B_4$, are independent of C and q.

$$B_1 = \frac{S_{sorp}k_f}{B_{fill}} \quad (14)$$

$$B_2 = \frac{S_{sorp}k_f}{B_{fill}F} \quad (15)$$

$$B_3 = \frac{S_{sorp}k_f}{(1-\phi)F} + k_{bind} \quad (16)$$

$$B_4 = \frac{S_{sorp}k_f}{(1-\phi)} \quad (17)$$

$$B_{fill} = \varphi + \frac{1-R_{fill}}{R_{fill}} \quad (18)$$

$S_{sorp}$ is the specific adsorption surface area
$k_f$ is a linear mass transfer coefficient
F is the partition relation coefficient
$k_{bind}$ is the coefficient for irreversible reaction/binding of the adsorbed fumigant in the grain kernel Example 1.4

Insect Mortality

It is known that the effect of phosphine on the mortality of grain insects is due to both the level of the phosphine concentration and the time of exposure. According to Collins et al. (2005) and Isa et al. (2016) an extinction indicator function e(x, t) could be defined as:

$$e(x, t) = \frac{1}{a_1} \int_0^t C(x, t)^{a_2} dt \quad (19)$$

The constants $a_1$ and $a_2$ are empirical constants and depend on the particular species and strain of insect. e(x, t) account for the period of exposure to phosphine that an insect has encountered. For a given point in the grain:
When e(x, t)<1 some measurable number of insects in the grain are still alive.
When e(x, t)>1 at least 99.9% of the insect population have been killed.
For rhyzopertha dominica $a_2=0.6105$ and $a_1=4.04$.

Example 1.5

Phosphine Source

A critical input of the exemplary model is the phosphine release rate or degassing rate from a phosphine dispenser. Metal phosphides ($Mg_3P_2$, AlP) are the most common form of phosphine source and are available in pellets, rounds, bags, etc. Degassing rates are a function of time, temperature, pressure and phosphine product and are evaluated by the following model:

Unified degassing model: Degassing rates can be described by a function of time with a dependence in temperature, pressure and phosphine product. A new equation of non-linear regression form may be used to describe the degassing rate of all phosphine fumigant products:

$$f(t) = 100A_1(1-\exp(-tA_2)) \quad (20)$$

$A_2$ coefficient is a function of phosphine fumigant product and relative humidity. A new coefficient ($A_1$) is created to take into account the slower degassing rates for low temperatures:

$$A_1 = 1 - \frac{(20 - T_{air})^2}{300} \quad (21)$$

$A_1$ and $A_2$ coefficients depend on commodity

Example 1.6

Calculation of Air Properties

In all calculations it is important to insert accurate values of the thermodynamic and transport properties of air at atmospheric pressure. The correlations proposed by McQuillan et al. (1984) are used:

$$\text{Density}: \rho = \frac{351.99}{T} + \frac{344.84}{T^2} \left[\frac{kg}{m^3}\right] \tag{22}$$

$$\text{Viscosity}: \mu = \frac{1.4592\, T^{3/2}}{109.10 + T} \left[10^{-6}\, \frac{Ns}{m^2}\right] \tag{23}$$

$$\text{Thermal conductivity}: k = \frac{2.3340 \cdot 10^{-3}\, T^{3/2}}{164.54 + T} \left[\frac{W}{mK}\right] \tag{24}$$

$$\text{Specific heat}: C_p = 1030.5 - 0.19975 T + 3.9734 \cdot 10^{-4}\, T^2 \left[\frac{J}{kg\,K}\right] \tag{25}$$

Thermal diffusivity: $\alpha =$ (26)

$$-4.3274 + 4.1190 \cdot 10^{-2} T + 1.5556 \cdot 10^{-4} T^2 \left[10^{-6} \frac{m^2}{s}\right]$$

Example 1.7

Boundary Conditions

In order to evaluate accurately the storage (computational domain) interaction with its surroundings, the following boundary conditions may be used:

Example 1.7.1

Mass Convective Boundary Condition

In order to calculate losses of phosphine from the silo walls/holes to the ambient air, the convective boundary condition may be used:

$$-D_m \frac{\partial C}{\partial x}\bigg|_{x=0} = h_m(C - C_{amb}) \tag{27}$$

For $h_m=0$ it becomes the zero gradient boundary condition. Since OpenFoam is not able to handle the above boundary condition, the installation of the swak4FOAM library may be necessary and specifically the use of groovybc boundary condition. $h_m$ is a function of silo geometry (cylinder, orthogonal), fluid medium (air, water) and fluid velocity (e.g. wind velocity). In convective mass transfer, the Churchill-Bernstein equation may be used to estimate the surface averaged Sherwood number for a cylinder in cross flow at various velocities:

$$Sh_D = \frac{h_m L}{D_m} = 0.3 + \frac{0.62 Re^{1/2} Sc^{1/3}}{[1 + (0.4/Sc)^{2/3}]^{1/4}} \left[1 + \left(\frac{Re}{282000}\right)^{5/8}\right]^{4/5} \tag{28}$$

Example 1.7.2

Thermal Convective Boundary Conditions

In order to calculate heat transfer on the boundary, the convective boundary condition may be used (Barreto et al., 2013)):

$$-k \frac{\partial C}{\partial x}\bigg|_{x=0} = h_c(T - T_{amb}) - \alpha_h G + \epsilon\sigma(T^4 - T_{sky}^4) \tag{29}$$

Where the second term of the right-hand side is the heat gain due to solar radiation and the third term is the net radiation heat loss rate for a hot object which is radiating energy to its cooler surrounding (Adelard et al. 1998).

$$T_{sky} = 0.0552 T_{amb} \sqrt{T_{amb}} \tag{30}$$

$$h_c = 10.45 - U_{wind} + 10\sqrt{U_{wind}} \tag{31}$$

* * *

Fumigant Dosage and Treatment Duration Optimization

In certain embodiments, it may be useful to obtain a relatively quick estimate of fumigant dosage for a given crop storage area. For example, a user may provide the dimensions and other characteristics of a crop storage area and the targeted pest via a user interface such as UI 900, and may initiate a quick estimate of the fumigant dosage by selecting "Calculate & Update" via treatment options 910. Such an estimate may be obtained using a lower-resolution approach compared to the model of process 1200, so that the estimate may be obtained more efficiently—e.g., by using one-dimensional cells, and not including heat transfer effects, not including velocity or pressure equations, and not including wind effects. This novel approach to efficiently estimating an effective fumigant dosage for a given product, crop storage area, and targeted pest is described below.

Figure 13:
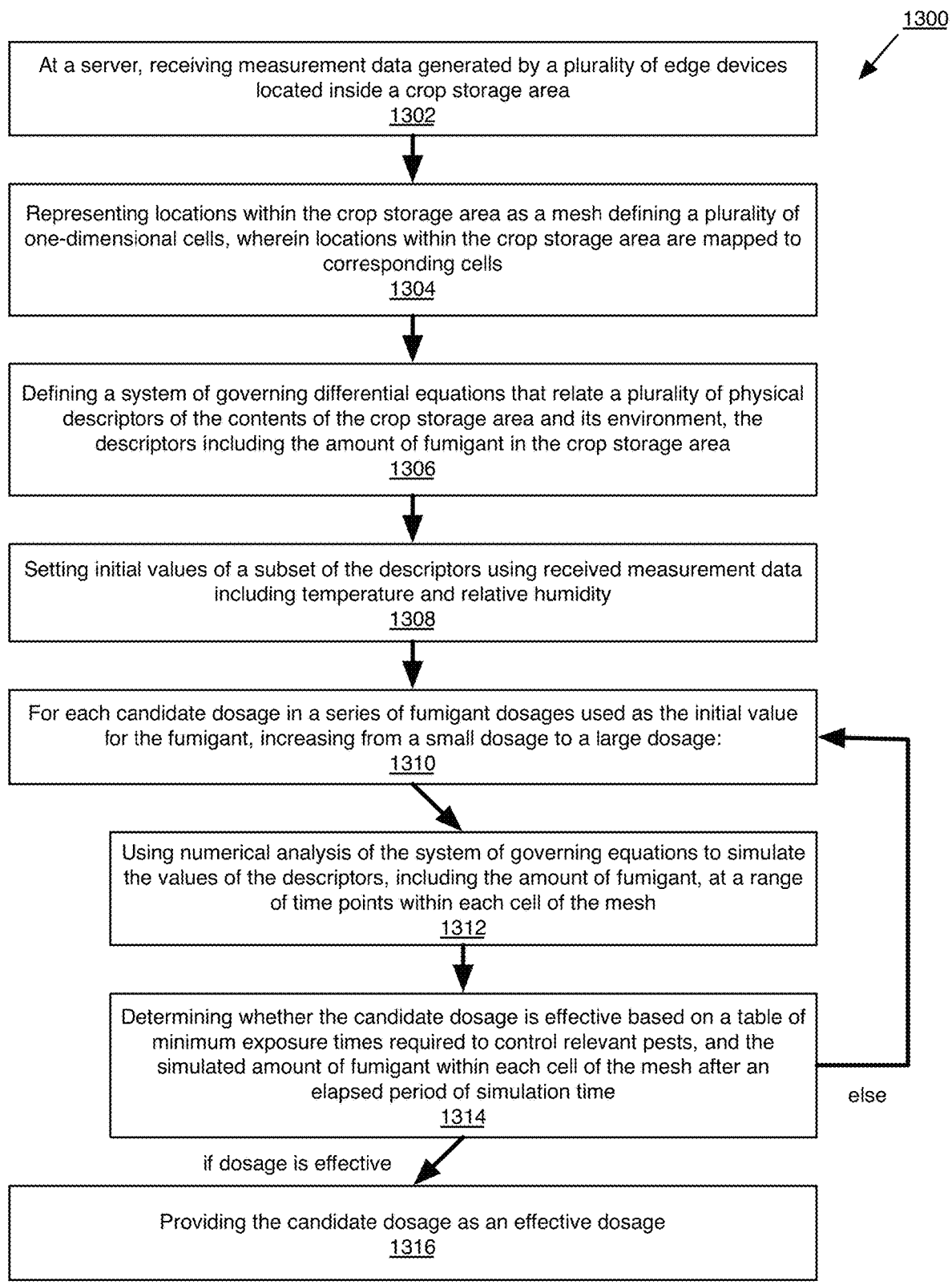
FIG. 13 shows a flow chart for an exemplary process concerning determining a fumigant dosage in accordance with some embodiments of the invention.

FIG. 13 shows a flow chart for an exemplary process 1300 concerning determining a fumigant dosage. First, a server (e.g., server 116) or user device 112 receives measurement data generated by a plurality of edge devices 102, where the edge devices may be positioned in various locations within a crop storage area 106 (1302). The measurement data may include, for example, temperature and/or relative humidity. In certain embodiments, temperature and relative humidity may be obtained from a third-party service, e.g., based on the geographic location of the crop storage area 106, or may be provided manually via a user interface such as UI 900.

Locations within the crop storage area may be represented as a mesh defining a plurality of one-dimensional cells, such that the physical locations in the crop storage area are mapped to corresponding cells of the mesh (1304). For example, the crop storage area may be mapped or projected onto a mesh of one-dimensional cells having an aggregate length corresponding to the longest dimension of the crop storage area, and the positions of edge devices may be projected accordingly onto the mesh. In certain embodiments, the three-dimensional space of the crop storage area may be represented in a one-dimensional model by discretizing only one of the three dimensions of the crop storage area, such as the length of the crop storage area.

A system of governing differential equations may be defined to relate a plurality of physical descriptors of the contents of the crop storage area and the environment of the crop storage area, wherein the descriptors include the amount of fumigant in the crop storage area (1306). For exemplary process 1300, the governing differential equations should model fumigant dispersion in a single dimension and may be a function of the type of product (crop), storage leaks (or gas tightness), metal phosphide type and weather conditions.

The initial values of certain physical descriptors may be set using edge device 102 measurements of temperature and/or relative humidity that correspond to the temperature and relative humidity measured at the location of the respective edge device, and thus characterizing the air and/or crop at the location (1308). Additional initial values of physical descriptors may be set based on, for example, known physical constants, the type of product, fumigant type and formulation, and weather conditions, the crop storage area volume, the fill percentage of the crop storage area, the quantity of product, the expected pest type, whether the pest type is resistant to the fumigant, and the expected leakage of the crop storage area.

While no effective dosage has been identified, and starting from a low dosage and increasing by a step with each iteration, the following steps 1312 and 1314 will be repeated (1310). For example, in the first iteration, the initial concentration of fumigant is set in accordance with a first low dosage of fumigant (i.e., a first candidate dosage). In a second iteration, the initial concentration of fumigant is set according to the sum of the first candidate dosage plus an increment (i.e., a second candidate dosage). As used in process 1300, the term effective dosage is a dosage of fumigant at the most remote point in the storage (where the remote point is distant from the fumigant dispenser(s)) resulting a concentration and exposure duration that is sufficient to control pests in the crop storage area. In certain embodiments, controlling pests may mean a 99% reduction in pests, 100% reduction in pests, or no measurable amount of pests remaining.

Numerical analysis of the governing differential equations may be used to simulate the values of the physical descriptors, including the amount of fumigant (starting from a candidate dose), at a range of time points within each cell of the mesh (1312). The simulated physical descriptors may include one or more of: sorption, fumigant degassing from a source, leakage, and fumigant diffusion.

A table of minimum exposure times and fumigant concentrations for controlling relevant pests may be used to determine whether the candidate dosage is effective, using the simulated fumigant concentration (at the most remote point in the storage area across a range of time points) to estimate the resulting fumigant concentration and duration for the candidate dosage (1314). If the candidate dosage is effective, the candidate dosage is reported as a recommended dosage for display at a user device, e.g. in response to a request from a user device via treatment options 910 (1316).

* * *

EXAMPLE 2 a one-dimensional CFD model for estimating an effective phosphine dosage

In order to calculate the appropriate phosphine dosage for a successful treatment the model described below may be used. The result (phosphine concentration on the most remote point of the storage) is a function of the commodity, storage leaks (or gas tightness), metal phosphide type and weather conditions.

Example 2.1

Governing Equations

The equations used by the model and that describe the phosphine concentration in a storage structure are the following:

$$\phi \frac{\partial C}{\partial t} = d \frac{\partial^2 C}{\partial x^2} - \phi B_1 C - \phi B_1 C + B_2 q + \phi Q_{source} - \phi R_{SV} Q_{loss} C \quad (32)$$

$$\frac{\partial q}{\partial t} = -B_3 q + \phi B_4 C \quad (33)$$

The phenomena taken into account in equations (32) and (33) are: sorption, phosphine degassing from a source, leakage (SVR is the surface to volume ratio), and phosphine diffusion.

In order to discretize equations (32) and (33), the Backward Euler method is used for the time derivative, which is a fully implicit scheme that provides accurate solutions and stable computations even for large time steps (compared to explicit schemes):

$$\phi \frac{C_i^{n+1} - C_i^n}{\Delta t} = d \frac{C_{i-1}^{n+1} + 2C_i^{n+1} - C_{i+1}^{n+1}}{(\Delta x)^2} -$$
$$\phi B_1 C_i^n - \phi B_1 C_i^n + B_2 q_i^n + \phi Q_{source,i}^n - \phi R_{sv} Q_{loss,i}^n C_i^n \rightarrow$$
$$C_i^{n+1} - C_i^n = \frac{\Delta t d}{\phi(\Delta x)^2}(C_{i-1}^{n+1} - 2C_i^{n+1} - C_{i+1}^{n+1}) + + \frac{\Delta t}{\phi}$$
$$(-\phi B_1 C_i^n - \phi B_1 C_i^n + B_2 q_i^n + \phi Q_{source,i}^n - \phi R_{sv} Q_{loss,i}^n C_i^n) \rightarrow$$
$$-\frac{\Delta t d}{\phi(\Delta x)^2} C_{i-1}^{n+1} + \left(1 + 2\frac{\Delta t d}{\phi(\Delta x)^2}\right) C_i^{n+1} - \frac{\Delta t d}{\phi(\Delta x)^2} C_{i+1}^{n+1} =$$
$$C_i^n + + \frac{\Delta t}{\phi}(-\phi B_1 C_i^n - \phi B_1 C_i^n + B_2 q_i^n + \phi Q_{source,i}^n - \phi R_{sv} Q_{loss,i}^n C_i^n)$$

The above equation system is tridiagonal which can be solved efficiently using the tridiagonal matrix algorithm. The solution can be obtained in O(n) operations instead of O(n³).

Eq. 33 has a simpler discretization form since it has no diffusion term:

$$\frac{q_i^{n+1} - q_i^n}{\Delta t} = -B_3 q_i^n + \phi B_4 C_i^n \rightarrow$$
$$q_i^{n+1} = q_i^n + (-B_3 q_i^n + \phi B_4 C_i^n)$$

Neumann boundary conditions may be used, since the value of the derivative is known $$\frac{\partial C}{\partial x} = 0.$$

Calculation of the dosage after an iteration: Brent's method may be used which is a root-finding algorithm combining the bisection method, the secant method and inverse quadratic interpolation. It has the reliability of bisection but it can be as quick as some of the less-reliable methods.

Example 2.2

Leakage Rate

In order to take into account leakages that may occur during a treatment, coefficient $Q_{loss}$[%/hour] is introduced. Additionally, a surface to volume ratio variable has been defined ($R_{sv}$) to evaluate storages with larger surfaces and potentially higher leakage rates.

Example 2.3

New Moisture Availability Function calculates available moisture and issues alerts if it's not sufficient. Moisture content [$H_2O$ gr/m3] available is calculated as a function of temperature and relative humidity:

$$MC = (5.018 + 0.32321 T_{air} + 0.0081847 T_{air}^2 + 0.00031243 T_{air}^3) r.h./100 \quad (34)$$

The demand of moisture according to the phosphine dosage, is equal to:

$$MC_d = 1.59 \cdot dosage[gr/m3] \quad (35)$$

Example 2.4

Unified Degassing Model as described in Example 1.

Example 2.5

Sorption as described in Example 1.

Example 2.6

Fumigation Protocols

Calculation of the appropriate phosphine dosage may be based on several fumigation protocols or according to user specifications.

For tobacco treatments the CORESTA (2013) protocol may be used:

TABLE 1

Minimum exposure-time required to achieve 100% control of all development stages of tobacco moth and susceptible cigarette beetle at 200 or 300 ppm phosphine at the bale/case centre.

| Tobacco Temperature | | Phosphine Concentration at the Bale/Case Centre | Minimum Exposure Time |
|---|---|---|---|
| [° C.] | [° F.] | [ppm] | [days] |
| 16-20 | 61-68 | 300 | 6 |
| >20 | >68 | 200 | 4 |

TABLE 2

Minimum exposure-time required to achieve 100% control of all development stages of resistant cigarette beetle at 300, 600 or 700 ppm phosphine at the bale/case center.

| Tobacco Temperature | | Phosphine Concentration at the Bale/Case Centre | Minimum Exposure Time |
|---|---|---|---|
| [° C.] | [° F.] | [ppm] | [days] |
| 16-20 | 61-68 | 300 | 12 |
| 20-25 | 68-77 | 300 | 12 |
|  |  | 700 | 10 |
| >25 | >77 | 300 | 12 |
|  |  | 600 | 6 |

For wheat treatments the GRDC protocol (2011) is considered: 1.5 gr $PH_3/m^3$.

Additionally, new fumigation protocols can be developed and used by compiling the results from bio-assay experiments and correlating fumigant dosage and duration with insect mortality.

Example 2.7

Oxidative Degradation

According to Robinson (1972) residual material may be expected to occur following phosphine fumigation of stored products. Phosphine oxide is reported as an intermediate in the room temperature polymerization of $PH_3$ and nitric oxide to solid $P_xH_y$. Robinson reported in his study that phosphorus residues of 2.5 ppm in a 1400 ppm atmosphere after 8 days of exposure (approximately 0.17%). Therefore the phenomenon of oxidative degradation is not taken into account in Example 2.

* * *

Stored Product Quality: Spoilage Protection

The process of crop storage often involves microbiological contamination and infestation. The microbial composition is of great importance, since at high moisture levels the microorganisms could grow and alter the properties of product. Product deterioration can also be related to respiration of the product itself and of the accompanying microorganisms.

Safe Product Storage Time

Described below are approaches for determining future moisture content and temperature in stored product, such as grain, and further using the moisture content and temperature to determine how long the product may continue to be safely stored in a particular crop storage area. Previous approaches for determining a safe storage time (1) assumed a static moisture content and temperature for the stored product—i.e., no change in moisture content and temperature over time; (2) applied a space-averaged assumption, in which the entire crop storage area is treated as having the same conditions/physical descriptors; (3) have not incorporated ambient weather conditions; and (4) have not combined advanced mathematical modeling with real-time sensor data. The approaches presented here determine, e.g., how moisture content and temperature have changed and are likely to change over time by incorporating transient conditions from sensor data, determine conditions for each location within a crop storage area in three dimensions, and incorporate ambient weather conditions in determining the safe storage time for a product.

Figure 15:
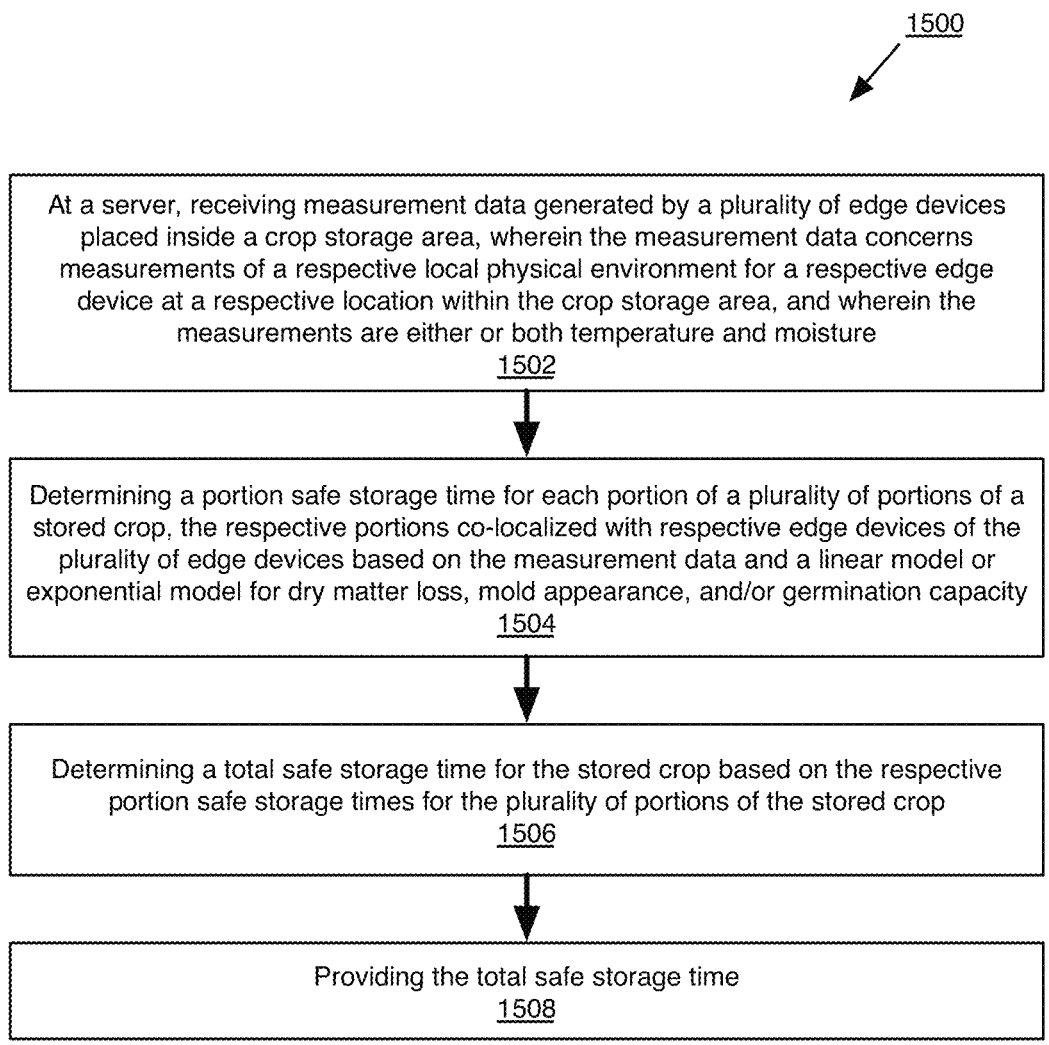
FIG. 15 shows a flow chart for an exemplary process concerning determining the safe storage time for a post-harvest crop in accordance with some embodiments of the invention.

FIG. 15 shows a flow chart for an exemplary process 1500 concerning determining the safe storage time for a post-harvest crop. First, a server (e.g., server 116) or user device 112 receives measurement data generated by a plurality of edge devices 102, where the edge devices may be positioned in various locations within a crop storage area 106 (1502). The measurement data may include, for example, concentration of $O_2$, concentration of $CO_2$, temperature, moisture, and/or relative humidity. In certain embodiments, temperature, moisture, and relative humidity may be obtained from a third-party service, e.g., based on the geographic location of the crop storage area 106, or may be provided manually via a user interface such as UI 900.

A portion safe storage time is determined for each portion of a plurality of portions of a stored crop, the respective portions co-localized with respective edge devices based on the measurement data, and a linear or exponential model for dry matter loss, mold appearance, and/or germination capacity (1504). As used in process 1500, a portion represents a portion of the total amount of stored crop that is associated with a respective edge device, and may be closer to the respective edge device than any other edge device in the crop storage area 106.

A total safe storage time for the stored crop is determined based on the respective portion safe storage times of step 1504 (1506). For example, the total safe storage time may be the shortest or earliest safe storage time selected from each portion safe storage time (e.g., the time associated with the portion that is predicted to spoil the soonest). In certain embodiments, the total safe storage time may be a weighted average of the portion safe storage times. In certain embodiments, a particular total safe storage time is determined for different types of spoilage, such as a visible mold safe storage time, a dry matter loss safe storage time, and a germination safe storage time. The total safe storage time(s) may be reported to a user device and displayed to a user, e.g., via the content panel 1104 of UI 1100.

In certain embodiments, if a portion safe storage time or a total safe storage time falls below a threshold, a component of system 100 may generate an instruction to take remedial action. For example, a remedial action may include generating a notification provided to a user to turn on fans; or automatically generating an instruction for an electrical system at the storage area to turn on a particular fan or set of fans.

* * *

EXAMPLE 3

Safe storage prediction for corn, wheat, and additional products

The following computational models described below may be used to predict safe storage time (SST), following the approach described in process 1500. They have a strong dependency on commodity, temperature (T), grain moisture content (Mw), dry matter loss (DML) and activity of water (aw).

Example 3.1

Model 1

Applicable to: Corn
Criterion: dry matter loss
Restrictions:
1<T[° C.]<24; 15<Mw %<30

Equation: $SST = v_1 + v_2 T + v_3 Mw + v_4 T^2 + v_5 TMw + v_6 Mw^2$

Coefficients: $v_1 = 3774.98$; $v_2 = -88.12$; $v_3 = -252.55$; $v_4 = 0.587$; $v_5 = 2.686$; $v_6 = 4.223$
Source: Kaleta and Gornicki (2013)

Example 3:2

Model 2

Applicable to: Wheat
Criterion: dry matter loss
Restrictions:
4<T[° C.]<40; 15<Mw %<24; 0.25<DML %<1

Equation: $SST = \exp(v_1 + v_2 T + v_3 Mw + v_4 DML)$

Coefficients: $v_1 = 6.490336$; $v_2 = -0.024165$; $v_3 = -0.163337$; $v_4 = 1.292568$
Source: Kaleta and Gornicki (2013)

Example 3.3

Model 3

Applicable to: Wheat, barley, oats, rye
Criterion: appearance of visible molds
Restrictions:
10<T[° C.]<25; 15<Mw %<24

Equation: $SST = \exp(v_1 + v_2 T + v_3 Mw)$

Coefficients:
Wheat:
$v_1 = 50.66928$; $v_2 = -0.272909$; $v_3 = -2.52755$
Barley:
$v_1 = 27.04320$; $v_2 = -0.174362$; $v_3 = -1.17856$
Oats:
$v_1 = 31.60300$; $v_2 = -0.201594$; $v_3 = -1.55997$
Rye:
$v_1 = 34.58371$; $v_2 = -0.283607$; $v_3 = -1.58288$
Source: Kaleta and Gornicki (2013)

Example 3:4

Model 4

Applicable to: Wheat, barley, oats, rye
Criterion: germination capacity
Restrictions:
10<T[° C.]<20; 11<Mw %<24

Equation: $SST = \exp(v_1 + v_2 T + v_3 Mw)$

Coefficients:
Wheat:
$v_1 = 12.28039$; $v_2 = -0.128973$; $v_3 = -0.473026$
Barley:
$v_1 = 13.12305$; $v_2 = -0.174000$; $v_3 = -0.452103$
Oats:
$v_1 = 13.96125$; $v_2 = -0.148378$; $v_3 = -0.604968$
Rye:
$v_1 = 10.13185$; $v_2 = -0.087999$; $v_3 = -0.426973$
Source: Kaleta and Gornicki (2013)

Example 3.5

Model 5

Applicable to: malting barley

Equation: $SST = \log\left(\frac{v_1}{T}\right) / \exp(v_2 + v_3 \, aw)$

Coefficients: $v_1 = 35.0$; $v_2 = -21.22$; $v_3 = 20.33$
Source: Fleurat-Lessard (2017)

Example 3.6

Model 6

Applicable to: Corn
Restrictions:
2<T[° C.]<32; 12<Mw %<24
Lookup table:

|       | Mw %  |       |       |       |       |       |       |       |       |
|-------|-------|-------|-------|-------|-------|-------|-------|-------|-------|
| T ° C. | 12   | 13    | 14    | 15    | 16    | 18    | 20    | 22    | 24    |
| 32    | 365+  | 365+  | 251   | 49    | 27    | 10    | 5     | 4     | 3     |
| 29    | 365+  | 365+  | 336   | 66    | 36    | 14    | 7     | 5     | 3     |
| 27    | 365+  | 365+  | 365+  | 87    | 47    | 18    | 9     | 6     | 4     |
| 24    | 365+  | 365+  | 365+  | 117   | 63    | 24    | 12    | 8     | 5     |
| 21    | 365+  | 365+  | 365+  | 157   | 85    | 32    | 16    | 10    | 7     |
| 18    | 365+  | 365+  | 365+  | 210   | 113   | 43    | 22    | 13    | 9     |
| 16    | 365+  | 365+  | 365+  | 278   | 150   | 57    | 28    | 17    | 11    |
| 13    | 365+  | 365+  | 365+  | 365+  | 226   | 86    | 38    | 22    | 14    |
| 10    | 365+  | 365+  | 365+  | 365+  | 339   | 130   | 50    | 29    | 19    |
| 7     | 365+  | 365+  | 365+  | 365+  | 365+  | 195   | 66    | 37    | 24    |
| 4     | 365+  | 365+  | 365+  | 365+  | 365+  | 293   | 88    | 48    | 30    |
| 2     | 365+  | 365+  | 365+  | 365+  | 365+  | 365+  | 115   | 62    | 39    |

Example 3.7

Insect Population Models

Temperature and moisture conditions in grain stores have an impact on the population growth rate of insect pests. Development rate increases from a lower threshold up to the optimum temperature and then declines rapidly. In order to evaluate insect population or growth rate, the following equations are used (Driscoll, 2000):

$$N(t + \Delta t) = N(t) e^{r_m \Delta t} \tag{36}$$

$$\frac{N(t)}{dt} = N_o r_m e^{r_m \Delta t} \tag{37}$$

$$r_m = f'(r.h.) e^{c_1 T} + \ln(c_2(T_m - T)) \tag{38}$$

$$f'(r.h.) = c_3 + c_4 r.h. + c_5 r.h.^2 \tag{39}$$

Where, $T_m$ is the mortality temperature, $N_o$ the initial insect population [number of insects/kg of grain]. The model is applicable for the following species: *Rhyzopertha dominica, Sitophilus oryzae, Oryzaephilus surinamensis, Tribolium castaneum*

Example 3.8

Determining grain condition for each location, within a crop storage area, using numerical modeling with sensor data and weather forecast integration In order to analyze grain storage condition and determine the change in concentration of $CO_2$ and temperature in silos the mathematical model proposed by Barreto et al. (2013) is used, but according to certain embodiments of the present invention it is adapted to three dimensions from their two-dimensional model. Such a three-dimensional model has not been attempted in previous reports due to computational expense and the difficulty in adapting such a system to three dimensions. Due to grain and insect respiration, $CO_2$ and temperature changes are both indicators for grain spoilage. The mathematical model takes into account the weather conditions locally and creates a coupled system in terms of temperature T, grain moisture content W, oxygen $O_2$ and carbon dioxide $CO_2$ concentrations:

$$c_p \rho_{bs} \frac{\partial T}{\partial t} = \nabla [k_b(\nabla T)] + \rho_{bs} L_g \frac{\partial W_g}{\partial t} + \rho_{bs} q_H Y_{CO_2} \tag{40}$$

$$\rho_{bs} \frac{\partial W_g}{\partial t} = \nabla [D_w(\eta \cdot \nabla W_g + \omega \cdot \nabla T)] + \rho_{bs} q_w Y_{CO_2} \tag{41}$$

$$\phi \frac{\partial CO_2}{\partial t} = \nabla [D_{CO_2}(\nabla CO_2)] + \rho_{bs} r_{CO_2} \tag{42}$$

$$\phi \frac{\partial O_2}{\partial t} = \nabla [D_{O_2}(\nabla O_2)] + \rho_{bs} r_{O_2} \tag{43}$$

Respiration may be modelled by the complete combustion of a typical carbohydrate. The rate of $CO_2$ production $r_{CO2}$ in $m^3\ s^{-1}\ kg^{-1}$ [dry matter] is given by:

$$r_{CO_2} = \frac{Y_{CO_2}}{1000} \frac{RT}{M_{CO_2} P_{at}} \tag{44}$$

$$r_{O_2} = r_{CO_2}$$

The boundary conditions related to the above equations (40)-(44) are given by:

$$-k_b \frac{\partial T}{\partial t} = h_c(T - T_{amb}) - \alpha G + \xi \sigma(T^4 - T_{sky}^4) \tag{45}$$

$$\sigma T_{sky}^4 = \xi_{sky} \sigma T_{amb}^4 \tag{46}$$

$$T = T_{soil}(y, t) \tag{47}$$

$$= T_1(y) + T_2 \exp\left(-y \sqrt{\frac{2\Psi}{D_{soil}}}\right) \left[\cos\left(\Psi t - y \sqrt{\frac{2\Psi}{D_{soil}}} - \varphi\right)\right]$$

$$\frac{\partial p_u}{\partial n} = 0 \Rightarrow \eta D_w \frac{\partial W_g}{\partial n} = -\omega D_w \frac{\partial T}{\partial n} \tag{48}$$

$$-D_{CO_2} \frac{\partial CO_2}{\partial n} = \frac{P_{CO_2} P_{atm}}{L}(CO_2 - CO_{2out}) \tag{49}$$

$$-D_{O_2} \frac{\partial O_2}{\partial n} = \frac{P_{O_2} P_{atm}}{L}(O_2 - O_{2out}) \tag{50}$$

The above boundary conditions (45)-(50) take into account solar radiation and convection to the surroundings, as well as the interaction between the soil and the bottom layer of the silo. Gas transfer through the plastic layer is modelled by defining an equivalent permeability of the plastic to $O_2$ and $CO_2$. Plastic is assumed impermeable to moisture transfer.

Figure 20:
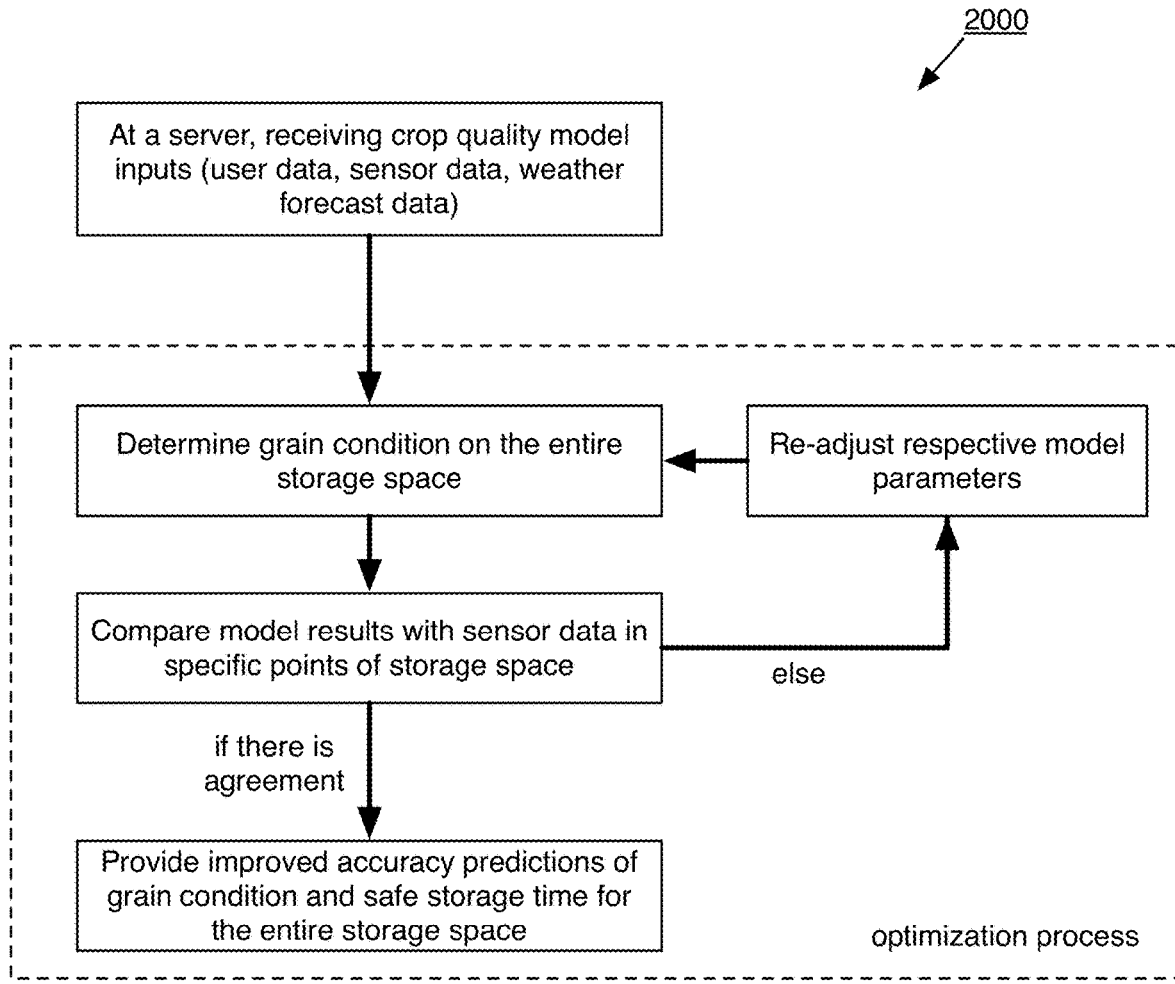
FIG. 20 shows a flow chart for an exemplary process concerning the improved predictions for grain condition and safe storage time.

The value of some parameters which are used as input to the model, often deviate from their typical values. For instance, thermal conductivity of a metal silo may vary due to corrosion or paint. This issue is overcome in embodiments by using real-time sensor data. As the storage period advances, model predictions are compared with sensor data at the locations where sensors are installed (defined in a three-dimensional space). An iterative optimization process 2000 is employed, to determine any changes in the input parameter values which improve the agreement between the model and sensor data. The outcome of this optimization process is a more accurate model prediction not only applicable to the specific sensor location(s) but by inference also applicable on the entire storage volume. FIG. 20 shows a flow chart concerning the optimization process 2000, according to a preferred embodiment.

* * *

Heat Treatments

A heat treatment is a popular method for eliminating pests in storage facilities. During this process, a crop storage area is heated for a specific time until most or all of pests have been eliminated.

Data Analysis for Heat Treatments

During a heat treatment, the system collects, in frequent intervals, measurements e.g., from edge devices 102 scattered inside the crop storage area/asset, and stores them in a database (e.g., at local data store 108 or remote data store 122). The measurements may be sent to an analytics system (application 120) for processing and prediction of future temperature values. The analytics system analyzes the data collected from past treatments and provides an estimation of the future temperature values inside the asset for each sensor. The system may present the time for successful pest elimination.

Figure 14:
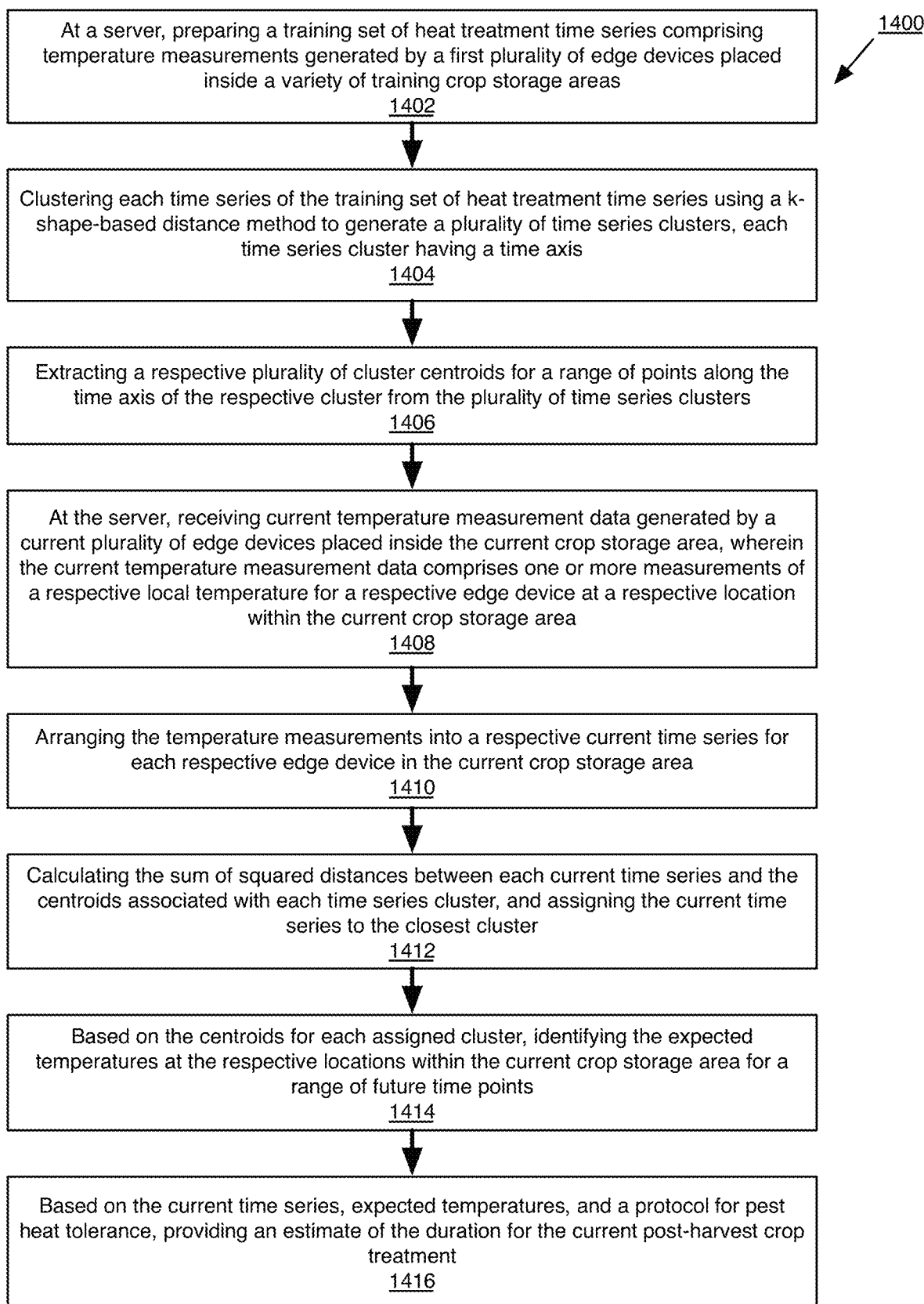
FIG. 14 shows a flow chart for an exemplary process concerning determining the duration of a heat treatment in accordance with some embodiments of the invention.

FIG. 14 shows a flow chart for an exemplary process 1400 concerning determining the duration of a heat treatment. First, a training set including a plurality of heat treatment time series is prepared, where each respective heat treatment time series is a set of temperature measurements and associated measurement times recorded from a single edge device 102 or temperature sensor (1402). The plurality of heat treatment time series should represent many different heat treatments, and it is desirable to include many different time series for each of the heat treatments. For example, the time series may represent measurements taken by edge devices distributed at positions throughout many different crop storage areas, for different types of crops, and during different seasons and at different geographic locations, in order to capture the full range of diversity of heat treatment time series and represent that diversity in the training set.

Figure 16:
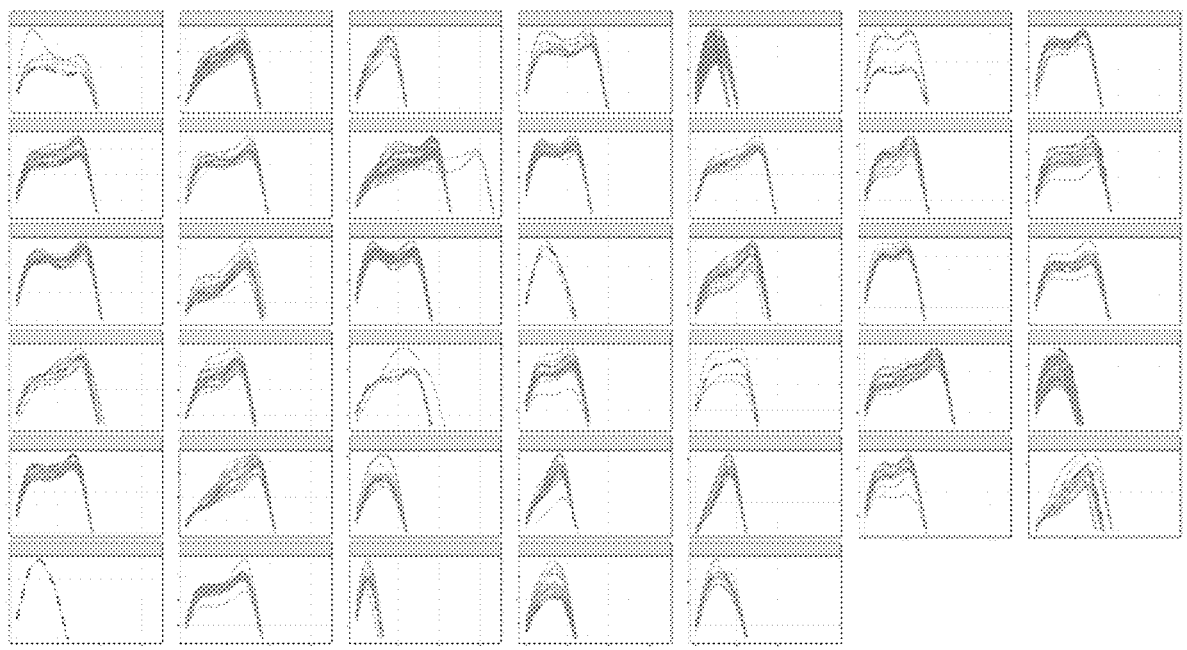
FIG. 16 shows exemplary clusters of temperature traces from heat treatments in accordance with some embodiments of the invention.

The training set of time series may be clustered using a k-shape-based distance method (1404). See, e.g., FIG. 16 showing 40 example resulting clusters of temperature traces from heat treatments.

A time series centroid may be extracted from each cluster to represent the respective cluster (1406) That is, the extracted centroid is a time series having the form of a series of temperatures associated with times. The centroids may be stored (e.g., in local data store 108 or remote data store 122) as exemplars of the expected course of a heat treatment.

An in-progress heat treatment applied to a current crop storage area may be evaluated based on the trained system. A server (e.g., server 116) or user device 112 receives measurement data generated by a plurality of edge devices 102, where the edge devices may be positioned in various locations within a current crop storage area 106 (1408). The measurement data includes temperature measurements and the times for the measurements. In certain embodiments, the received measurement data may include thermal camera images.

Figure 17:
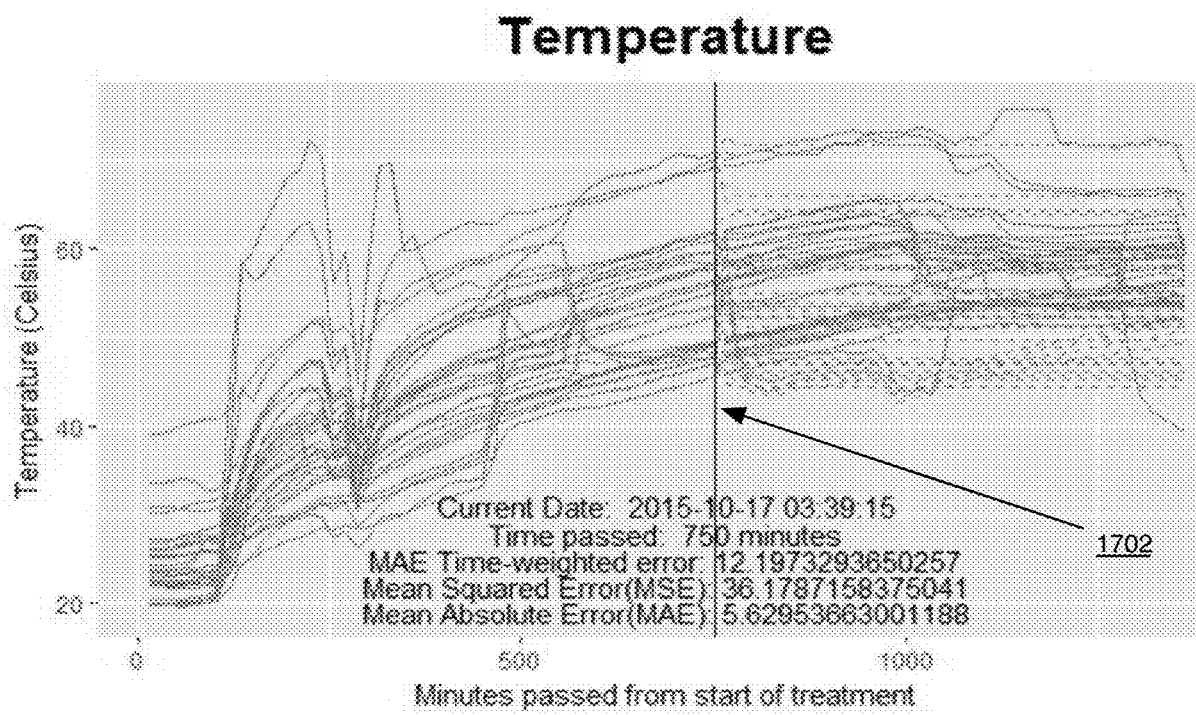
FIG. 17 shows exemplary temperature traces from heat treatments in accordance with some embodiments of the invention.

The received temperature data is arranged into a respective current time series for each respective edge device in the current crop storage area (1410). The most similar time series centroid in the training set may be identified for each current time series, e.g., by calculating the sum of squared distances between each current time series and a database of exemplar centroids (1412). The expected course of future temperatures for each current time series may be estimated in accordance with the most similar centroid (1414). Based on the heat tolerance (temperature, duration) for the targeted pest, the predicted course of treatment may be estimated as having with the shape of the most similar centroids (1416). For example, if four edge devices are used in a current heat treatment, four centroids will be identified to represent the expected course of treatment for the four positions in the crop storage area where the four edge devices are located. In certain embodiments, the range of the duration of treatment may be reported using the centroids associated with the best and worst edge node positions and corresponding measurements. For example, the shape of the centroid, as aligned to the current temperature series, may be used to generate a projection of the expected temperature at various future time points, and the durations of the expected temperatures may be used to determine the amount of time until the targeted pest cannot survive. See, e.g., FIG. 17, showing exemplary temperature traces from heat treatments and predicted temperatures, described below in connection with Example 4.

* * *

EXAMPLE 4

Heat Treatments

Example 4.1

Predictive Analytics

Example 4.1.1

Training

One of the primary tasks of the predictive analytics approach is to perform accurate predictive analytics of sensor data to estimate future values and to achieve that a number of tasks need to be completed. Firstly, we gather historical data to serve as a training set. We perform dataset reduction by choosing a sampling rate of, preferably, 15 minutes since the collected data has varying time intervals and the sensors' data length may differ. By implementing data manipulation functions, time series are "forced" to have similar time and length readings for all sensors. Information is not lost from problematic sensors, for instance with a small amount of readings (malfunctioning) have already been removed. Some time series have missing values which are interpolated filling with additional data and consequently the series resulting are of the same length and calculated metrics are of specific timestamps (15 minutes, 1 hour, etc.). In the second step, as time series data exhibit noise the need for removing it and producing smoother data is important. The method used is low-pass filtering and preferably the type of signal processing filter is the Butterworth filter. After applying filtering to raw data, a new smoothest version of sensor readings is obtained.

As the number of edge devices may be large, the time-series data are often high dimensional and slow down the analysis process. Clustering entails grouping temperature time series that are similar to each other and extracts information from unlabeled data.

Multiple distance measures can be used to find clusters among time series by calculating the distance among them.

A shape-based distance method, where sequences exhibit similar patterns (the distance is the smallest), are grouped into the same cluster based on their shape similarity regardless of differences in amplitude and phase. This distance is based on coefficient normalization and cross-correlation distance (J. Paparrizos, L. Gravano, 2016) between pairs of sensors among time series without having necessarily the same length. So, as a first step the cross-distance matrix is calculated and z-normalized as the distance works better that way for the sensors readings inside the training set. In the next step, time series clustering is performed choosing k clusters and calculating the centroids using partition methods where each cluster has a centroid that is also time series. (See FIG. 16.) This results in multiple clusters and their centroids that stored for further usage. To conclude the training process, a small amount of historical data serves as a testing set where the performance of the clustering, the centroids and the prediction process is tested, resulted in an error that needs to be as small as possible, meaning that the predicted values and the actual are close.

Example 4.1.2

Prediction

When a new treatment takes place, new time series arrive from heat treatments, the new data are preprocessed as mentioned and grouped to already existed clusters based on the k-shaped distance method that minimizes the sum of squared distances between new series and the clusters' centroids. When the new time series have been successfully grouped into new clusters the clusters' centroids are used to predict new values.

FIG. 17 shows exemplary temperature traces from heat treatments. Prediction time indicator 1702 separates actual measurements from predicted temperatures based on the shape of the most similar centroids—i.e., marker 1702 indicates the current time in minutes from beginning of the treatment when the future temperature courses were determined.

Example 4.2

Impact of Heat on Pests

Pests can survive the exposure of high temperatures for a limited amount of time. As heat tolerance differs between pests, the system may be configured to determine the best elimination protocol for each pest. Based on each protocol, the temperature should stay above a certain threshold for specific time to achieve a successful elimination of pests. The heat tolerance of pests for each elimination protocol is described in the following tables:

| Heat tolerance of tribolium confusum - Kansas state university 2008 | | | | | | |
|---|---|---|---|---|---|---|
| Temperature threshold(Celsius) | 46 | 48 | 50 | 52 | 54 | 56 |
| Time for 99% elimination(mins) | 700 | 198 | 90 | 47 | 32 | 19.9 |

| Heat tolerance of tribolium castaneum - Kansas state university 2003 | | | | | |
|---|---|---|---|---|---|
| Temperature threshold(Celsius) | 50 | 54 | 58 | 60 | |
| Time for 99% elimination(mins) | 572 | 208 | 76 | 66 | |

| Heat tolerance of hemidactylus turcicus - CSL 2005 | | | | |
|---|---|---|---|---|
| Temperature threshold(Celsius) | 47 | 49 | 51 | 53 |
| Time for 99% elimination(mins) | 420 | 120 | 30 | 18 |

| Heat tolerance of bed bugs - University of Florida 2009 | | | | | |
|---|---|---|---|---|---|
| Temperature threshold(Celsius) | 41 | 43 | 45 | 47 | 49 |
| Time for 99% elimination(mins) | 100 | 25 | 4 | 2.5 | 1 |

* * *

Nomenclature and Abbreviations

AR aspect ratio AR=H/L
C phosphine concentration
$C_{ref}$ reference concentration
$C_p$ specific heat under constant pressure [J kg$^{-1}$ K$^{-1}$]
$D_a$ Darcy number [m$^2$ s$^{-1}$] $D_a$=K/L$^2$
$D_m$ binary diffusion coefficient [m$^2$ s$^{-1}$]
$D_w$ effective diffusivity parameter for water vapour
dp solid particle diameter [m]
F is the partition relation coefficient
g magnitude of the gravitational acceleration, g=9.81 [m s$^{-2}$]
G solar radiation [W m$^{-2}$]
Gr thermal Grashof number Gr=g β H$^3_{in}$ΔT/ν$^2$
$Gr_c$ solutal Grashof number Gr=g β H$^3_{in}$ΔC/ν$^2$
$h_c$ heat transfer coefficient
$h_m$ mass transfer coefficient
H characteristic height [m]
k thermal conductivity [W m$^{-1}$ K$^{-1}$]
K permeability of the porous matrix [m$^2$], the ability to allow the fluid to flow through
$k_f$ linear mass transfer coefficient used in sorption modelling
k binding coefficient for irreversible reaction/binding of the adsorbed fumigant in the grain kernel
L characteristic length [m]
Le Lewis number Le=Sc/Pr
$L_g$ latent heat of vaporisation of moisture in grain
MW molecular weight [kg mol$^{-1}$]
N Buoyancy ratio N=$Gr_c$/Gr
p pressure [N m$^{-2}$]
Pr Prandtl number Pr=ν/α
$R_{fill}$ is the filling ratio of stored product to asset volume
Ra Rayleigh number Ra=gβ($T_h$-$T_c$)H$^3$/(να)
Re Reynolds number based on the height of the tank Re=$u_{ref}$L/ν
Sc Schmidt number Sc=ν/Dm
$S_{sorp}$ specific adsorption surface area
t physical time [s]
T local temperature [K]

$T_{ref}$ reference temperature [K]
u, v Cartesian velocity components [m s$^{-1}$]
$U_{wind}$ wind velocity [m s$^{-1}$]
x, y coordinate distance along the length and height of the tank [m]

Greek Symbols
α thermal diffusivity [m$^2$ s$^{-1}$]
$α_h$ absorptivity
β volumetric expansion coefficient for temperature $$\beta = -\frac{1}{\rho}\left(\frac{\partial \rho}{\partial T}\right)_p \ [K^{-1}]$$

$β_c$ species expansion coefficient, [m$^3$ kg$^{-1}$]
ε emissivity
η change in partial pressure due to change in the moisture content at constant temperature
μ dynamic viscosity
ν kinematic viscosity [m$^2$ s$^{-1}$]
ρ density [kg m$^{-3}$]
$ρ_{bs}$ dry bulk density [kg m$^{-3}$]
φ porosity $$\varphi = \frac{\text{pore volume}}{\text{total volume}}$$

σ Stefan Boltzmann coefficient
τ tortuosity, $$\tau = \frac{\text{curve length}}{\text{distance between ends}}$$

ω change in partial pressure due to change in temperature at constant moisture content

REFERENCES

L. Adelard, F. Pignolet-Tardan, T. Mara, P. Lauret, F. Garde, H. Boyer, Sky temperature modelisation and applications in building simulation, Renewable Energy, Volume 15, Issue 1, 1998, Pages 418-430.

A. Barreto, A. Rita, G. Analia, B. Ricardo, Analysis of storage conditions of a wheat silo-bag for different weather conditions by computer simulation. Biosystems Engineering 116, pp. 497-508 (2013).

P. J. Collins, G. J. Daglish, H. Pavic, and R. A. Kopittke. Response of mixed-age cultures of phosphine-resistant and susceptible strains of lesser grain borer, rhyzopertha dominica, to phosphine at a range of concentrations and exposure periods. Journal of Stored Products Research, 41:373-385, 2005.

CORESTA, Phosphine fumigation parameters for the control of cigarette beetle and tobacco moth. CORESTA guide No 2 (October 2013).

J. A Darby. A kinetic model of fumigant sorption by grain using batch experimental data. Pest Management Science, 64(5):519-526, 2008.

R Driscoll, B. C Longstaff, S Beckett, Prediction of insect populations in grain storage, Journal of Stored Products Research, Volume 36, Issue 2 (2000).

F. Fleurat-Lessard, Integrated management of the risks of stored grain spoilage by seedborne fungi and contamination by storage mould mycotoxins—An update, Journal of Stored Products Research, Volume 71 (2017).

W. He, W. Lv, and J. Dickerson. Gas transport in oxide fuel cells. Springer International Publishing, New York, USA (2014).

G R D C, Fumigating with phosphine, other fumigants and controlled atmospheres, A grains industry guide. Grains Research and Development Corporation (2011).

Z. M. Isa, T. W. Farrell, G. R. Fulford, and N. A. Kelson. Mathematical modelling and numerical simulation of phosphine flow during grain fumigation in leaky cylindrical silos. Journal of Stored Products Research, 67:28-40, 2016.

A. Kaleta, and K. Gornicki. Criteria of Determination of Safe Grain Storage Time—A Review, Advances in Agrophysical Research, chapter 12 (2013)

McQuillan, F. J., Culham, J. R., and Yovanovich, M. M., Properties of Dry Air as One Atmosphere, Microelectronics Heat Transfer Lab., Rept. UW/M HTL 8406 G-01, Univ. of Waterloo, Waterloo, ON, Canada, 1984.

S. Neethirajan, D. S. Jayas, N. D. G. White, and H. Zhang. Investigation of 3d geometry of bulk wheat and pea pores using x-ray computed tomography images. Computers and Electronics in Agriculture, 63(2):104-111, 2008.

J. R. Robinson. Residues containing phosphorus following phosphine treatment: Measurement by neutron activation. Journal of Stored Products Research, 8(1):19-26, 1972.

L. Shen and Z. Chen. Critical review of the impact of tortuosity on diffusion. Chemical Engineering Science, 62(14):3748-3755, 2007.

John Paparrizos, Luis Gravano, k-Shape: Efficient and Accurate Clustering of Time Series, ACM SIGMOD Record, v.45 n.1, 2016.

Figure 19:
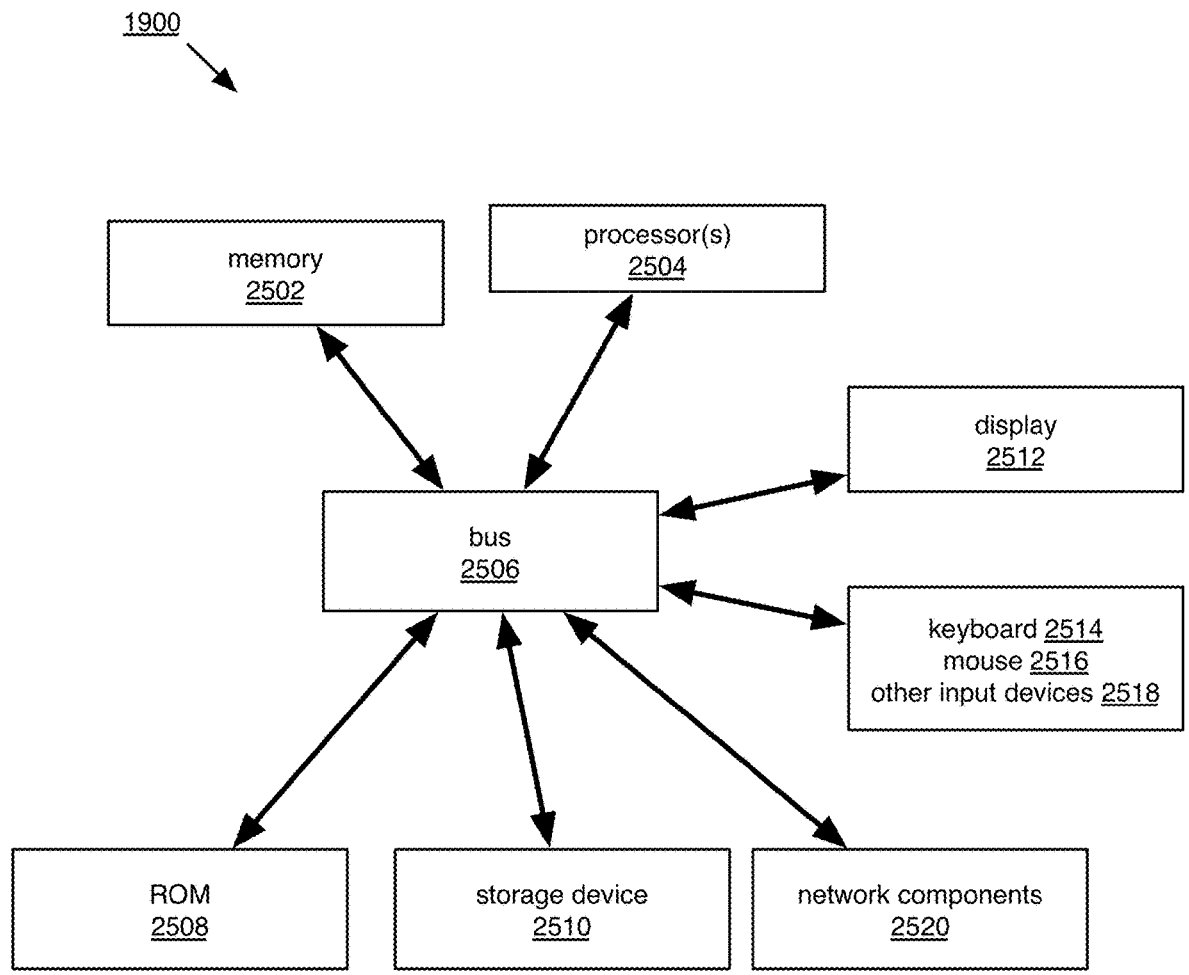
FIG. 19 depicts a block diagram of an exemplary computing system in accordance with some embodiments of the invention.

FIG. 19 depicts a block diagram of an exemplary computing system 1900 that is representative any of the computer systems or electronic devices discussed herein. Note that not all of the various computer systems have all of the features of system 1900. For example, systems may not include a display inasmuch as the display function may be provided by a client computer communicatively coupled to the computer system or a display function may be unnecessary.

System 1900 includes a bus 2506 or other communication mechanism for communicating information, and processor(s) 2504 coupled with the bus 2506 for processing information. Computer system 1900 also includes a main memory 2502, such as a random-access memory or other dynamic storage device, coupled to the bus 2506 for storing information and instructions to be executed by processor 2504. Main memory 2502 also may be used for storing temporary variables or other intermediate information during execution of instructions to be executed by processor 2504.

System 1900 includes a read-only memory 2508 or other static storage device coupled to the bus 2506 for storing static information and instructions for the processor 2504. A storage device 2510, which may be one or more of a hard disk, flash memory-based storage medium, magnetic tape or other magnetic storage medium, a compact disc (CD)-ROM, a digital versatile disk (DVD)-ROM, or other optical storage medium, or any other storage medium from which processor 2504 can read, is provided and coupled to the bus 2506 for storing information and instructions (e.g., operating systems, applications programs and the like).

Computer system 1900 may be coupled via the bus 2506 to a display 2512 for displaying information to a computer user. An input device such as keyboard 2514, mouse 2516, or other input devices 2518 may be coupled to the bus 2506 for communicating information and command selections to the processor 2504. Communications/network components 2520 may include a network adapter (e.g., Ethernet card), cellular radio, Bluetooth radio, NFC radio, GPS receiver, and antennas used by each for communicating data over various networks, such as a telecommunications network or LAN.

The processes referred to herein may be implemented by processor 2504 executing appropriate sequences of computer-readable instructions contained in main memory 2502. Such instructions may be read into main memory 2502 from another computer-readable medium, such as storage device 2510, and execution of the sequences of instructions contained in the main memory 2502 causes the processor 2504 to perform the associated actions. In alternative embodiments, hard-wired circuitry or firmware-controlled processing units (e.g., field programmable gate arrays) may be used in place of or in combination with processor 2504 and its associated computer software instructions to implement the invention. The computer-readable instructions may be rendered in any computer language including, without limitation, Python, Objective C, C#, C/C++, Java, Javascript, assembly language, markup languages (e.g., HTML, XML), and the like. In general, all of the aforementioned terms are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 1900 or a similar electronic computing device, that manipulates and transforms data represented as physical (electronic) quantities within its registers and memories into other data similarly represented as physical quantities within its memories or registers or other such information storage, transmission or display devices.

Embodiments

Embodiment A. A system for post-harvest crop quality and pest management employing sensor devices that transmit signals wirelessly from inside product storage areas.

The system of Embodiment A whereby sensor devices are fumigant sensing devices that form mesh data networks.

The system of Embodiment A whereby sensor devices are temperature or humidity sensing devices that form mesh data networks.

The system of Embodiment A whereby sensor devices are housed in plastic enclosures sealed using one or more O-rings to protect the electronics from corrosion by chemicals such as phosphine and employ a magnetic or similar contactless method for activation and deactivation.

The system of Embodiment A whereby sensor devices can be calibrated by the end user using a cloud-connected appliance that records calibration coefficients in the cloud and uses coefficients from multiple devices to improve overall sensor accuracy and device useful life.

The system of Embodiment A whereby sensor devices employ an antenna designed as a short inverted-L monopole with an orthogonal meander line top plate having a total line length of approximately a quarter wavelength, to provide for improved transmission characteristics from inside crop storage areas.

Embodiment B. A method for post-harvest crop quality and pest management employing sensor devices that transmit signals wirelessly from inside product storage areas.

The method of Embodiment B that fuses data from said sensor devices with data from weather stations to improve predictions.

The method of Embodiment B that employs clustering data analytics methods to provide predictions of pest treatment duration, success and other key metrics.

The method of Embodiment B that employs CFD simulations to provide predictions and prescriptions of pest treatments such as phosphine fumigations.

The method of Embodiment B that employs CFD simulations and computational models to provide predictions of stored product quality such as safe storage time, insect infestation risk, dry matter loss and germination capacity.

The method of Embodiment B that employs CFD simulations and data from sensors to provide predictions of physical quantities in-between sensor locations.

The method of Embodiment B that employs CFD simulations and data from sensors to predict the worst-case fumigant levels inside stored products in a fumigation treatment.

The method of Embodiment B implemented as a cloud-hosted application and accessible from mobile, wearable and desktop devices.

Embodiment 1. An edge device, comprising:
a plastic housing comprising:
a cap having a first threaded portion and a plurality of vents configured to allow air passage from the environment of the edge device into an environment-exposed compartment;
an upper housing having a second threaded portion, a third threaded portion, and an upper surface containing a sensor opening; and
a lower housing having a fourth threaded portion, wherein the first threaded portion of the cap is configured to mate with the second threaded portion of the upper housing, and the third threaded portion of the upper housing is configured to mate with the fourth threaded portion of the lower housing, such that when assembled the cap and the upper housing define the environment-exposed compartment, and the upper housing and the lower housing define a sealed compartment;
an electrochemical gas sensor comprising a sensor cell and a sensor circuit board, wherein the electrochemical gas sensor is partially disposed within the sealed compartment and is fixed in a position abutting the upper surface of the upper housing such that the sensor cell protrudes into the sensor opening to form a surface of the environment-exposed compartment;
one or more upper rubber o-rings circumferentially disposed around a portion of the electrochemical gas sensor that protrudes into the environment-exposed compartment to create a seal that abuts the sensor opening of the upper housing;
a main circuit board disposed within the sealed compartment and communicatively coupled to the electrochemical gas sensor, the main circuit board having a plurality of mounted components respectively coupled to a battery, a reed switch, an antenna, and radio frequency (RF) circuitry;
a magnet disposed on a first plastic ring, and a second plastic ring, wherein the first plastic ring is configured to rotate around the fourth threaded portion of the lower housing, disposed between the upper housing and the second plastic ring, such that the magnet is arranged to interact with the reed switch by the rotation of the first plastic ring, and the second plastic ring is configured to mate with the fourth threaded portion of the lower housing; and one or more lower rubber o-rings disposed at the interface between the upper housing and the lower housing.

Embodiment 2. The edge device of embodiment 1, wherein the housing is formed from an acetal plastic, such as an acetal copolymer.

Embodiment 3. The edge device of embodiment 1, wherein the vents are micro holes.

Embodiment 4. The edge device of embodiment 1, wherein the battery is a lithium thionyl chloride battery.

Embodiment 5. The edge device of embodiment 1, wherein the monopole antenna is a short inverted-L monopole antenna with an orthogonal meander line top plate having a total line length of a nominal quarter wavelength.

Embodiment 6. The edge device of embodiment 1, wherein the first plastic ring is rotatable between two detents representing "on" and "off" positions.

Embodiment 7. The edge device of embodiment 1, wherein the number of upper rubber o-rings is two.

Embodiment 9. A system comprising:
a plurality of edge devices and a gateway device, the plurality of edge devices and the gateway device collectively forming a mesh network, the gateway device communicatively connected to the internet, the plurality of edge devices arranged within a storage area and the gateway device positioned outside of the storage area, each edge device of the plurality comprising:
a housing having a cylindrical or bell-shaped form, the housing comprising a battery pack compartment and a second compartment, wherein the battery pack compartment is separated from the second compartment by a physical safety layer;
one or more sensor devices disposed within the second compartment of the housing, each sensor device configured to obtain a measurement of the local physical environment, and wherein a sensor cell of the one or more sensor devices is positioned adjacent to one or more vents in the housing such that the sensor cell is in fluid contact with the local physical environment;
a network component disposed within the housing and communicatively coupled to the one or more sensor devices, the network component configured to communicate as a node in the mesh network, wherein the network component comprises an antenna; and
a battery pack disposed within the battery pack compartment of the housing.

Embodiment 10. The system of embodiment 9, wherein a first one of the one or more sensor devices comprises the sensor cell, the sensor cell configured for sensing a gas, the gas selected from the group consisting of phosphine, carbon dioxide, and oxygen.

Embodiment 11. The system of embodiment 9, wherein the one or more sensor devices comprise a sensor device selected from the group consisting of a thermal camera, a moisture sensor, a humidity sensor, and a temperature sensor.

Embodiment 12. The system of embodiment 9, wherein the antenna is a short inverted-L monopole antenna with an orthogonal meander line top plate having a total line length of a nominal quarter wavelength.

Embodiment 13. The system of embodiment 9, wherein the housing further comprises two or more o-rings to seal sensor-component-associated openings of the housing.

Embodiment 14. The system of embodiment 9, wherein the housing further comprises a magnetic switch configured to control activation of the one or more sensor devices.

Embodiment 15. A method for managing post-harvest fumigation treatment to exterminate pests, comprising:

i. at a server, receiving measurement data generated by a plurality of edge devices placed inside a storage area, wherein the measurement data concerns measurements of a respective local physical environment for a respective edge device at a respective location within the storage area;

ii. representing locations within the storage area as a mesh defining a plurality of three-dimensional cells, wherein locations within the storage area are mapped to corresponding cells;

iii. defining a system of governing differential equations that relate a plurality of physical descriptors of the contents of the storage area and the environment of the storage area, wherein the plurality of physical descriptors includes the amount of fumigant in the storage area;

iv. simulating the amount of fumigant within each cell of the mesh by steps comprising:
setting initial values of a subset of the plurality of physical descriptors using a portion of the received measurement data, wherein the portion of the received measurement data comprises temperature and relative humidity; and
using numerical analysis of the system of governing differential equations to approximate the values of the physical descriptors at a range of time points, including the amount of fumigant;

v. optionally, assessing treatment completion by:
determining the amount of living pests for the range of time points, based on the simulated amounts of fumigant in the mesh across the range of time points;
identifying the time points associated with an amount of living pests that is equal to or less than an acceptable amount based on the inferred amount of living pests and inferring a corresponding time remaining for a complete fumigation treatment; and
providing a continuously updated estimate for the time remaining for a complete fumigation treatment.

Embodiment 16. The method of embodiment 15, wherein the system of governing differential equations includes a representation of heat transfer effects, and a mass boundary condition that depends on wind.

Embodiment 17. The method of embodiment 15, wherein the method further comprises:
identifying discrepancies between the simulated and actual amounts of fumigant, wherein the portion of the received measurement data further comprises fumigant amounts and the associated locations for the measurements;
based on the identified discrepancies, identifying a location for increasing fumigant within the storage area that is optimal for reducing the time remaining for a complete fumigation treatment based on the simulated concentrations of fumigant; and
providing an instruction to add or move a fumigant dispenser to the optimal location.

Embodiment 18. The method of embodiment 15, wherein the method further comprises:
determining the difference between the simulated and actual amounts of fumigant, wherein the portion of the received measurement data further comprises fumigant amounts and the associated locations for the measurements, wherein the difference is calculated as an average across the measurements from different locations within the storage area;
if the difference indicates that the actual amounts are significantly lower than the predicted amounts, providing an instruction to place a specified additional fumigant dose into the storage area; otherwise, not providing the instruction.

Embodiment 19. The method of embodiment 15, wherein the storage area is a silo, shipping container, or vessel hold.

Embodiment 20. The method of embodiment 15, wherein receiving measurement data generated by a plurality of edge devices comprises receiving real-time updates of measurement data.

Embodiment 21. The method of embodiment 15, wherein the physical descriptors further comprise temperature and relative humidity.

Embodiment 22. A method for determining post-harvest crop fumigation dosage, comprising:

at a server, receiving measurement data generated by a plurality of edge devices placed inside a storage area, wherein the measurement data concerns measurements of a respective local physical environment for a respective edge device at a respective location within the storage area;

representing locations within the storage area as a mesh defining a plurality of one-dimensional cells, wherein locations within the storage area are mapped to corresponding cells;

defining a system of governing differential equations that relate a plurality of physical descriptors of the contents of the storage area and its environment, wherein the plurality of physical descriptors includes the amount of fumigant in the storage area;

simulating the amount of fumigant within each cell of the mesh by steps comprising:

setting initial values of a subset of the plurality of physical descriptors using a portion of the received measurement, wherein the portion of the received measurement data comprises temperature and relative humidity; and for each candidate dosage in a series of fumigant dosages used as the initial value for the fumigant, increasing from a small dosage to a large dosage, while no effective dosage has been identified:

using numerical analysis of the system of governing differential equations to simulate the values of the physical descriptors, including the amount of fumigant, at a range of time points within each cell of the mesh;

determining whether the candidate dosage is effective based on a table of minimum exposure times required to control relevant pests, and the simulated amount of fumigant within each cell of the mesh after an elapsed period of simulation time; and providing the candidate dosage as an effective dosage if it is determined to be effective, otherwise continuing with an increased fumigant dosage.

Embodiment 23. The method of embodiment 22, wherein the storage area is a silo, shipping container, or vessel hold.

Embodiment 24. The method of embodiment 22, wherein receiving measurement data generated by a plurality of edge devices comprises receiving real-time updates of measurement data.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for managing post-harvest stored crop quality and marketability, comprising:

between a group of edge devices deployed within a crop storage area, establishing a wireless ad hoc network and transmitting from a gateway device of the wireless ad hoc network measurement data concerning measurements of local physical environment parameters including either or both temperature and relative humidity within the crop storage network made by sensors of the edge devices, wherein said gateway device collects the measurement data from the edge devices and transmits said measurement data using a fog agent executing on the gateway device, at a server, receiving the measurement data transmitted by the fog agent of the gateway device, processing the received measurement data using a rules engine configured to assess the measurement data according to one or more user-defined rule sets for automated execution of predetermined actions according to said rule sets, and determining by the server a portion safe storage time for each portion of a plurality of portions of a stored crop at said crop storage area, the respective portions co-localized with respective ones of said edge devices of the plurality of edge devices, said portion safe storage times determined according to the measurement data and a linear model or exponential model for dry matter loss, mold appearance, or germination capacity;

determining by the server a total safe storage time for the stored crop based on the respective portion safe storage times for the plurality of portions of the stored crop;

presenting the total safe storage time as process analytics item of a post-harvest crop management user interface of a client application executing on a client workstation communicably coupled to said server; and responsive to a determination that the total safe storage time is below a predetermined threshold, said server automatically initiating a remedial action to affect environmental conditions of the crop storage area.

2. The method of claim 1, wherein determining the portion safe storage time for each portion of the plurality of portions is further based on a three-dimensional mathematical model and the measurement data, wherein the measurement data includes both temperature and relative humidity.

3. The method of claim 1, wherein determining the portion safe storage time is additionally based on external weather conditions at a geographic site for the storage area as coupled to the temperature, moisture, oxygen, and carbon dioxide concentrations inside the storage area.

4. The method of claim 1, wherein determining the portion safe storage time is additionally based on an insect population reported by a plurality of edge devices.

5. The method of claim 1, wherein the total safe storage time is determined as the earliest portion safe storage time or a weighted average of the portion safe storage times.

* * * * *